United States Patent
Lee

(10) Patent No.: US 10,829,760 B2
(45) Date of Patent: *Nov. 10, 2020

(54) NUCLEIC ACID MOLECULES INDUCING RNA INTERFERENCE, AND USES THEREOF

(71) Applicant: OliX Pharmaceuticals, Gyeonggi-Do (KR)

(72) Inventor: Dong Ki Lee, Seoul (KR)

(73) Assignee: Olix Pharmaceuticals, Inc., Gyeonggi-Do (KR)

( * ) Notice: Subject to any disclaimer, the term of this patent is extended or adjusted under 35 U.S.C. 154(b) by 8 days.

This patent is subject to a terminal disclaimer.

(21) Appl. No.: 16/220,030

(22) Filed: Dec. 14, 2018

(65) Prior Publication Data

US 2019/0177732 A1 Jun. 13, 2019

Related U.S. Application Data

(60) Continuation of application No. 15/474,615, filed on Mar. 30, 2017, now Pat. No. 10,214,744, which is a division of application No. 13/880,670, filed as application No. PCT/KR2011/006632 on Sep. 7, 2011, now Pat. No. 9,637,742.

(30) Foreign Application Priority Data

Oct. 22, 2010 (KR) .................. 10-2010-0103701
Jun. 27, 2011 (KR) .................. 10-2011-0062504

(51) Int. Cl.
| | |
|---|---|
| C12N 15/113 | (2010.01) |
| A61K 31/7088 | (2006.01) |
| C12N 15/11 | (2006.01) |
| A61K 31/7105 | (2006.01) |
| A61K 31/711 | (2006.01) |

(52) U.S. Cl.
CPC ...... *C12N 15/1135* (2013.01); *A61K 31/7088* (2013.01); *A61K 31/711* (2013.01); *A61K 31/7105* (2013.01); *C12N 15/111* (2013.01); *C12N 15/113* (2013.01); *C12N 2310/12* (2013.01); *C12N 2310/14* (2013.01); *C12N 2310/3519* (2013.01); *C12N 2310/50* (2013.01)

(58) Field of Classification Search
CPC ............ A61K 31/7088; A61K 31/7105; A61K 31/711; C12N 15/111; C12N 15/113; C12N 15/1135; C12N 2310/12; C12N 2310/14; C12N 2310/50; C12N 2310/3519
USPC ............. 435/6.1, 91.1, 91.31; 536/23.1, 24.5
See application file for complete search history.

(56) References Cited

U.S. PATENT DOCUMENTS

| | | | |
|---|---|---|---|
| 5,837,258 A | 11/1998 | Grotendorst | |
| 7,078,196 B2 | 7/2006 | Tuschl et al. | |
| 7,691,997 B2 | 4/2010 | Khvorova et al. | |
| 7,700,541 B2 | 4/2010 | Tanaka et al. | |
| 8,410,260 B2 | 4/2013 | Collin-Djangone et al. | |
| 8,614,309 B2 | 12/2013 | Feinstein et al. | |
| 8,802,733 B2 | 8/2014 | Ganesan et al. | |
| 8,822,428 B2 | 9/2014 | Collin-Djangone et al. | |
| 8,980,273 B1 | 3/2015 | Clube | |
| 9,453,226 B2 | 9/2016 | Ambati et al. | |
| 9,637,742 B2 | 5/2017 | Lee | |

(Continued)

FOREIGN PATENT DOCUMENTS

| | | |
|---|---|---|
| CN | 101835789 A | 9/2010 |
| CN | 102719432 | 10/2012 |

(Continued)

OTHER PUBLICATIONS

Ambati et al., "Mechanisms of Age-Related Macular Degeneration," Neuron, 75: 26-39 (2012).
Chang et al., "The design, preparation, and evaluation of asymmetric small interfering RNA for specific gene silencing in mammalian cells." Methods Mol Biol. 2013; 942:135-52.
Hong et al., "Effect of the guide strand 3'-end structure on the gene-silencing potency of asymmetric siRNA," Biochemical Journal, (2014), 461(3): 427-434.
Huang et al., "Targeting the ANGPT-TIE2 Pathway in Malignancy," Nat Rev Cancer, 10: 575-585 (2010).
Hwang, "Development of Cell-Penetrating Asymmetric Interfering RNA Targeting Connective Tissue Growth Factor," Journal of Investigative Dermatology, (2016), 136(11), 2305-2313.

(Continued)

*Primary Examiner* — Jane J Zara
(74) *Attorney, Agent, or Firm* — Morgan, Lewis & Bockius LLP

(57) ABSTRACT

The present invention relates to an RNAi-inducing nucleic acid molecule having a new structure and the use thereof, and more particularly to a novel nucleic acid molecule having a structure comprising a first strand, which is 24-121 nt in length and comprises a region complementary to a target nucleic acid, and a second strand which is 13-21 nt in length and has a region that binds complementarily to the region of the first strand, which is complementary to the target nucleic acid, so that the nucleic acid molecule inhibits the expression of a target gene with increased efficiency, and to a method of inhibiting the expression of a target gene using the nucleic acid molecule. The nucleic acid molecule structure of the present invention increases the efficiency with which the nucleic acid molecule inhibits the target gene. Alternatively, the nucleic acid molecule of the present invention can either increase the ability of the siRNA to bind to the target gene or cause synergistic cleavage, by introduction of antisense DNA, antisense RNA, ribozyme or DNAzyme, thereby increasing the efficiency with which the nucleic acid molecule inhibits the target gene. In addition, when the nucleic acid molecule according to the present invention is used, the efficiency with which the target gene is inhibited can be maintained for an extended period of time. Accordingly, the RNAi-inducing nucleic acid molecule of the present invention can be effectively used for the treatment of cancer or viral infection in place of conventional siRNA molecules.

19 Claims, 14 Drawing Sheets

Specification includes a Sequence Listing.

(56) References Cited

U.S. PATENT DOCUMENTS

| | | | |
|---|---|---|---|
| 9,707,235 B1 | 7/2017 | Ambati | |
| 10,059,949 B2 | 8/2018 | Lee et al. | |
| 10,064,801 B2 | 9/2018 | Hong et al. | |
| 10,125,362 B2 | 11/2018 | Hong | |
| 10,214,744 B2* | 2/2019 | Lee | C12N 15/111 |
| 10,358,648 B2 | 7/2019 | Lee et al. | |
| 2004/0138163 A1 | 7/2004 | McSwiggen et al. | |
| 2004/0180351 A1 | 9/2004 | Giese et al. | |
| 2004/0266707 A1 | 12/2004 | Leake et al. | |
| 2005/0119202 A1 | 6/2005 | Kreutzer et al. | |
| 2005/0282188 A1 | 12/2005 | Haeberli et al. | |
| 2006/0069050 A1 | 3/2006 | Rana | |
| 2006/0094032 A1 | 5/2006 | Fougerolles et al. | |
| 2006/0105976 A1 | 5/2006 | Soutschek et al. | |
| 2006/0134787 A1 | 6/2006 | Zamore et al. | |
| 2006/0142228 A1 | 6/2006 | Ford et al. | |
| 2006/0160123 A1 | 7/2006 | Quay | |
| 2007/0218495 A1 | 9/2007 | Birmingham et al. | |
| 2007/0275914 A1 | 11/2007 | Manoharan et al. | |
| 2008/0125386 A1 | 5/2008 | Rana et al. | |
| 2008/0188430 A1 | 8/2008 | Usman et al. | |
| 2009/0004668 A1 | 1/2009 | Chen et al. | |
| 2009/0012022 A1 | 1/2009 | Milner et al. | |
| 2009/0130751 A1 | 5/2009 | Davidson et al. | |
| 2009/0191625 A1 | 7/2009 | Khvorova et al. | |
| 2009/0208564 A1 | 8/2009 | Li et al. | |
| 2010/0197023 A1 | 8/2010 | Leake et al. | |
| 2010/0254945 A1 | 10/2010 | Ge et al. | |
| 2010/0291681 A1 | 11/2010 | Khvorova et al. | |
| 2011/0028534 A1 | 2/2011 | Shepard et al. | |
| 2011/0054160 A1 | 3/2011 | Manoharan et al. | |
| 2011/0237647 A1 | 9/2011 | Shirasawa et al. | |
| 2011/0237648 A1 | 9/2011 | Khvorova et al. | |
| 2011/0251258 A1 | 10/2011 | Samarsky et al. | |
| 2011/0263680 A1 | 10/2011 | Khvorova et al. | |
| 2011/0269816 A1 | 11/2011 | Kaspar et al. | |
| 2012/0016011 A1 | 1/2012 | Pickering et al. | |
| 2012/0238017 A1 | 9/2012 | Lee et al. | |
| 2013/0011922 A1 | 1/2013 | Quay et al. | |
| 2013/0035368 A1 | 2/2013 | Avkin-Nachum et al. | |
| 2013/0115613 A1 | 5/2013 | Madiraju et al. | |
| 2013/0123342 A1 | 5/2013 | Brown | |
| 2013/0131142 A1 | 5/2013 | Libertine et al. | |
| 2013/0190387 A1 | 7/2013 | Feinstein | |
| 2013/0273657 A1 | 10/2013 | Lee | |
| 2013/0317080 A1 | 11/2013 | Rajeev et al. | |
| 2014/0094501 A1 | 4/2014 | Puri et al. | |
| 2014/0227266 A1 | 8/2014 | Lee et al. | |
| 2014/0249304 A1 | 9/2014 | Lee et al. | |
| 2014/0328903 A1 | 11/2014 | Santel et al. | |
| 2014/0350068 A1 | 11/2014 | Feinstein et al. | |
| 2015/0111948 A1 | 4/2015 | Hong | |
| 2015/0184163 A1 | 7/2015 | Wilson et al. | |
| 2016/0017056 A1 | 1/2016 | Clube | |
| 2016/0122764 A1 | 5/2016 | Chae et al. | |
| 2016/0319278 A1 | 11/2016 | Khvorova et al. | |
| 2017/0298358 A1 | 10/2017 | Lee et al. | |
| 2017/0369882 A1 | 12/2017 | Khvorova et al. | |

FOREIGN PATENT DOCUMENTS

| | | |
|---|---|---|
| EP | 2631291 A2 | 8/2013 |
| JP | 2008535496 A | 9/2008 |
| JP | 2011500003 A | 1/2011 |
| JP | 2011101655 A | 5/2011 |
| JP | 2012502991 | 2/2012 |
| JP | 2012061007 A | 3/2012 |
| KR | 20070028363 A | 3/2007 |
| KR | 10-2009-0065880 | 6/2009 |
| KR | 101207561 | 12/2012 |
| WO | WO 0244321 A2 | 6/2002 |
| WO | WO-02/055693 | 7/2002 |
| WO | WO-2005/062937 A2 | 7/2005 |
| WO | WO-2005/079533 A2 | 9/2005 |
| WO | WO-2007/022470 A2 | 2/2007 |
| WO | WO-2007/041282 A2 | 4/2007 |
| WO | WO-2007/128477 A2 | 11/2007 |
| WO | WO 2008109377 A1 | 9/2008 |
| WO | WO2009020344 | 2/2009 |
| WO | WO-2009029688 A2 | 3/2009 |
| WO | WO 2009029690 A1 | 3/2009 |
| WO | WO-2009078685 A2 | 6/2009 |
| WO | WO2009105260 | 8/2009 |
| WO | WO-2010/033247 A2 | 3/2010 |
| WO | WO 2010090762 A1 | 8/2010 |
| WO | WO-2011/108682 A1 | 9/2011 |
| WO | WO201119887 | 9/2011 |
| WO | WO-2012/053841 A2 | 4/2012 |
| WO | WO2012078536 | 6/2012 |
| WO | WO2012118911 | 9/2012 |
| WO | WO2014043291 | 3/2014 |
| WO | WO2015002513 | 1/2015 |
| WO | WO2015015498 | 2/2015 |
| WO | WO2015171641 | 11/2015 |
| WO | WO2017017523 | 2/2017 |
| WO | WO2017085550 | 5/2017 |
| WO | WO2017134525 | 8/2017 |
| WO | WO2017134526 | 8/2017 |
| WO | WO2017178883 | 8/2017 |
| WO | WO2018004284 | 1/2018 |
| WO | WO2018146557 | 8/2018 |

OTHER PUBLICATIONS

Jo et al., "Selection and optimization of asymmetric siRNA targeting the human c-MET gene," Mol Cell, 32:(6) 543-548 (2011).

Joshi et al., "siRNA: novel therapeutics from functional genomics," Biotechnology and Genetic Enginnering Reviews (2014) vol. 30, No. 1, pp. 1-30.

Kelly et al., "Cell Type-Specific Regulation of Angiogenic Growth Factor Gene Expression and Induction of Angiogenesis in Nonischemic Tissue by a Constitutively Active Form of Hypoxia-inducible Factor 1," Circ Res, 93: 1074-1081 (2003).

Lee et al., "Asymmetric RNA Duplexes as Next Generation RNAi Inducers," Gene Silencing: Theory, Techniques and Applications, (2010), pp. 343-348.

Patel et al., "A Novel Protective Role for the Innate Immunity Toll-Like Receptor 3 (TLR3) in the Retina via Stat3," Mol Cell Neurosci, 63: 38-48 (2014).

Ui-Tei et al., "Guidelines for the selection of highly effective siRNA sequences for mammalian and chick RNA interference," (2004), Nucleic Acids Research, vol. 32, pp. 936-948.

Yuan et al., "Asymmetric siRNA: New Strategy to Improve Specificity and Reduce Off-Target Gene Expression", Human Gene Therapy 23:521-532 (2013).

Anonymous, "Biology & Biotechnology: Scientific Frontiers in the 21st Century (The 1st Symposium for the Global Research Laboratory (GRL) Program of Korea," 20-11 (2010).

Grimm, "Small silencing RNAs: State of the art," Advanced Drug Delivery Reviews, 61: 672-703 (2009).

Kim et al., "Synthetic dsRNA Dicer substrates enhance RNAi potency and efficacy," Nature Biotechnology, 23: 222-226 (2005).

Kubo et al., "Modified 27nt dsRNAs with Dramatically Enhanced Stability in Serum and Long-Term RNAi Activity," Oligonucleotides, 17: 445-464 (2007).

Lima et al., "Human Dicer Binds Short Single-strand and Double-strand RNA with High Affinity and Interacts with Different Regions of the Nucleic Acids," The Journal of Biological Chemistry, 284: 2535-2548 (2009).

Marques et al., "A structural basis for discriminating between self and nonself double-stranded RNAs in mammalian cells," Nature Biotechnology, 24: 559-565 (2006).

Sano et al., "Effect of asymmetric terminal structures of short RNA duplexes on the RNA interference activity and strand selection," Nucleic Acids Research, 36: 5812-5821 (2008).

Sun et al., "Asymmetric RNA duplexes mediate RNA interference in mammalian cells," Nature Biotechnology, 26: 1379-1382 (2008).

Yang et al., "Hent recognizes 21-24 nt small RNA duplexes and deposits a methyl group onto the 2' OH of the 3' terminal nucleotide," Nucleic Acids Research, 34: 667-675 (2006).

(56) References Cited

OTHER PUBLICATIONS

Bolcato-Bellemin et al., "Sticky Overhangs Enhance siRNA-mediated Gene Silencing," Proc Natl Aca Sci USA, 104(41): 16050-16055 (Oct. 3, 2007).
Bramsen et al., "Improved Silencing Properties Using Small Internally Segmented Interfering RNAs," Nucleic Acids Res, 35: 5886-5897 (2007).
Bushati et al., "MicroRNAs in Neurodegeneration," Current Opin Neurobiol, 18: 292-296 (2008).
Caplen et al., "Specific Inhibition of Gene Expression by Small Double-Stranded RNAs in Invertebrate and Vertebrate Systems," Proc Natl Acad Sci USA, 98(17): 9742-9747 (2001).
Chang et al., "Asymmetric Shorter-Duplex siRNA Structures Trigger Efficient Gene Silencing With Reduced Nonspecific Effects," Mol Ther, 17: 725-732 (2009).
Chang et al., "Structural diversity repertoire of gene silencing small interfering RNAs," Nucleic Acid Therapeutics, 21(3):125-31 (2011).
Chiu et al., "siRNA Function in RNAi: A Chemical Modification Analysis," RNA, 9: 1034-1048 (2003).
Doench et al., "siRNAs Can Function as miRNAs," Gene Dev, 17(4): 438-442 (2003).
Doench et al., "Specificity of MicroRNA Target Selection in Translation Repression," Gene Dev, 18: 504-511 (2004).
Elbashir et al., "Duplexes of 21-nucleotide RNAs Mediate RNA Interference in Cultured Mammalian Cells," Nature, 411: 494-498 (May 24, 2001).
Elbashir et al., "Functional Anatomy of siRNAs for Mediating Efficent RNAi in *Drosophila melanogaster* Embryo Lysate," EMBO J, 20(23): 6877-6888 (2001).
Fire et al., "Potent and Specific Genetic Interference by Double-Stranded RNA in Caenorhabditis Elegans," Nature, 391: 806-811 (1998).
Fire, "RNA-triggered Gene Silencing," Trends Genet, 15(9): 358-363 (1999).
Hammond, "Post-Transcriptional Gene Silencing by Double-Stranded RNA," Nature Reviews, 2: 110-119 (2001).
Hines et al., "Synthetic Construct *Homo sapiens* Clone FLH019006. 01L Connective Tissue Growth Factor (CTGF) mRNA, Partial cds," GenBank: Accession No. AY890732, Mar. 21, 2005.
*Homo sapiens* connective tissue growth factor (CTGF), mRNA, NM_001901.1, published on Apr. 23, 2016, accessed and retrieved from www.ncbi.nlm.nih.gov on Apr. 21, 2016. total 12 printout pages.
Jackson et al., "Expression Profiling Reveals Off-Target Gene Regulation by RNAi," Nat Biotechnol, 21: 635-637 (2003).
Jang et al., "Gene Delivery From Polymer Scaffolds for Tissue Engineering," Expert Rev Med Devic, 1(1): 127-138 (2004).

Jeong et al., "siRNA conjugate delivery systems," Bioconjugate Chem, 20:5-14 (2009).
Kore et al., "Chemical modification of synthetic RNAi agents and in vivo delivery techniques," Curr Bioactive Compounds, 4:6-14 (2008).
Kulkarni et al., "Evidence of Off-Target Effects Associated with Long dsRNAs in *Drosophila melanogaster* Cell-Based Assays," Nat Methods, 3: 833-838 (2006).
Li et al., "Inhibition of Connective Tissue Growth Factor by siRNA Prevents Liver Fibrosis in Rats," J Gene Med, 8: 889-900 (May 2, 2006).
Luo et al., "Inhibition of Connective Tissue Growth Factor by Small Interfering RNA Prevents Renal Fibrosis in Rats Undergoing Chronic Allograft Nephropathy," Transplant P, 40: 2365-2369 (Sep. 2008).
Martinez et al., "Singe-Stranded Antisense siRNAs Guide Target RNA Cleavage in RNAi," Cell, 110: 563-574 (Sep. 6, 2002).
Opalinska et al., "Nucleic-acid Therapeutics: Basic Principles and Recent Applications," Nature Rev, 1(7): 503-514 (2002).
Paroo et al., "Challenges for RNAi in vivo," Trends in Biotech, 22(8): 390-394 (2004).
Raouane et al., "Lipid conjugated oligonucleotides: a useful strategy for delivery," Bioconjugate Chem, 23:1091-104 (2012).
Rose et al., "Functional Polarity is Introduced by Dicer Processing of Short Substrate RNAs," Nucleic Acids Res, 33: 4140-4156 (2005).
Sharp, "RNA-Interference-2001," Gene Dev, 15: 485-490 (2001).
Sioud et al., "Cationic Liposome-mediated Delivery of siRNAs in Adult Mice," Biochem Bioph Res Co, 312: 1220-1225 (Dec. 26, 2003).
Sisco et al., "Antisense Inhibition of Connective Tissue Growth Factor (CTGF/CCN2) mRNA Limits Hypertrophic Scarring Without Affecting Wound Healing in Vivo," Wound Repair Regen, 16: 661-673 (Sep.-Oct. 2008).
Song et al., "The Crystal Structure of the Argonaute2 PAZ Domain Reveals an RNA Binding Motif in RNAi Effector Complexes," Nat Struct Biol, 10(12): 1026-1032 (Dec. 2003).
Soutschek et al., "Therapeutic Silencing of an Endogenous Gene by Systemic Administration of Modified siRNAs," Nature, 432: 173-178 (2004).
Ui-Tei et al., "Essential Notes Regarding the Design of Functional siRNAs for Efficient Mammalian RNAi," J Biomed Biotechnol, 2006: 1-8 (2006).
Vasdudevan et al., "Switching from Repression to Activation: MicroRNAs Can Up-Regulate Translation," Science, 318: 1931-1934 (2007).
Wang et al., "Nucleation, Propagation and Cleavage of Target RNAs in Ago Silencing Complexes," Nature, 461: 754-762 (Oct. 8, 2009).
Zamore, "RNA Interference: Listening to the Sound of Silence," Nat Struct Biol, 8(9): 746-750 (2001).

* cited by examiner

CTNNB1-2siRNA
S  5'-CUAUCAAGAUGAUGCAGAACU-3'    SEQ ID NO: 1
AS 3'-UUGAUAGUUCUACUACGUCUU-5'   SEQ ID NO: 2
Dz339 DNAzyme
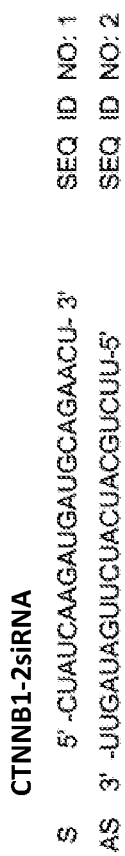
SEQ ID NO: 3
Dz339-AS hybrid
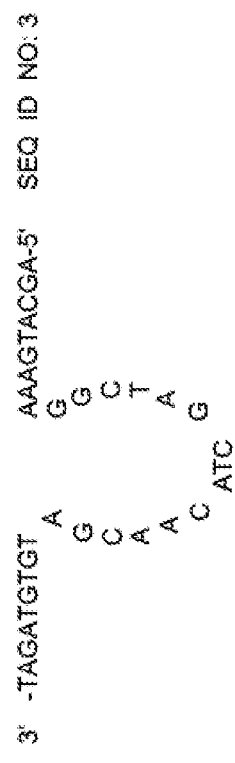
SEQ ID NO: 1
SEQ ID NO: 4
FIG. 4

| | | | |
|---|---|---|---|
| KRAS | 19+2 | 5'-GGAAGCAAGUAGUAAUGAUU-3' (S)<br>3'-UUCCUUCGUUCAUCAUUACU-5' (AS) | SEQ ID NO:5<br>SEQ ID NO:6 |
| | 21S+5d | 5'-GGAAGCAAGUAGUAAUGAUU-3' (S)<br>3'-aggatGUCCUUCGUUCAUCAUUAACU-5' (AS) | SEQ ID NO:5<br>SEQ ID NO:7 |
| | 21S+5c | 5'-GGAAGCAAGUAGUAAUGAUU-3' (S)<br>3'-tacgaGUCCUUCGUUCAUCAUUAACU-5' (AS) | SEQ ID NO:5<br>SEQ ID NO:8 |
| | 21S+10d | 5'-GGAAGCAAGUAGUAAUGAUU-3' (S)<br>3'-tcctaaggatGUCCUUCGUUCAUCAUUAACU-5' (AS) | SEQ ID NO:5<br>SEQ ID NO:9 |
| | 21S+10c | 5'-GGAAGCAAGUAGUAAUGAUU-3' (S)<br>3'-accagtacgaGUCCUUCGUUCAUCAUUAACU-5' (AS) | SEQ ID NO:5<br>SEQ ID NO:10 |
| | 21S+15d | 5'-GGAAGCAAGUAGUAAUGAUU-3' (S)<br>3'-ttatctcctaaggatGUCCUUCGUUCAUCAUUAACU-5' (AS) | SEQ ID NO:5<br>SEQ ID NO:11 |
| | 21S+15c | 5'-GGAAGCAAGUAGUAAUGAUU-3' (S)<br>3'-ttggcaccagtacgaGUCCUUCGUUCAUCAUUAACU-5' (AS) | SEQ ID NO:5<br>SEQ ID NO:12 |
| | 21S+15d-mut | 5'-GGAAGCAAGUAGUUUAACAUU-3' (S)<br>3'-ttatctcctaaggatGUCCUUCGUUCAUCAAAUUGU-5' (AS) | SEQ ID NO:13<br>SEQ ID NO:14 |

FIG. 5

| | | | |
|---|---|---|---|
| KRAS | asiRNA | 5'-AGCAAGUAGUAAUUGA-3' (S)<br>3'-UUCCUUCGUUCAUCAUUAACU-5' (AS) | SEQ ID NO: 17<br>SEQ ID NO: 18 |
| | 16S+5d | 5'-AGCAAGUAGUAAUUGA-3' (S)<br>3'-aggatgUUCCUUCGUUCAUCAUUAACU-5' (AS) | SEQ ID NO: 17<br>SEQ ID NO: 19 |
| | 16S+5c | 5'-AGCAAGUAGUAAUUGA-3' (S)<br>3'-tacgagUUCCUUCGUUCAUCAUUAACU-5' (AS) | SEQ ID NO: 17<br>SEQ ID NO: 20 |
| | 16S+10d | 5'-AGCAAGUAGUAAUUGA-3' (S)<br>3'-tcctaaggatgUUCCUUCGUUCAUCAUUAACU-5' (AS) | SEQ ID NO: 17<br>SEQ ID NO: 21 |
| | 16S+10c | 5'-AGCAAGUAGUAAUUGA-3' (S)<br>3'-accagtacgagUUCCUUCGUUCAUCAUUAACU-5' (AS) | SEQ ID NO: 17<br>SEQ ID NO: 22 |
| | 16S+15d | 5'-AGCAAGUAGUAAUUGA-3' (S)<br>3'-ttatctcctaaggatgUUCCUUCGUUCAUCAUUAACU-5' (AS) | SEQ ID NO: 17<br>SEQ ID NO: 23 |
| | 16S+15c | 5'-AGCAAGUAGUAAUUGA-3' (S)<br>3'-ttggcaccagtacgagUUCCUUCGUUCAUCAUUAACU-5' (AS) | SEQ ID NO: 17<br>SEQ ID NO: 24 |

FIG. 8

| | | | |
|---|---|---|---|
| KRAS | 21S+10r | 5'-GGAAGCAAGUAGUAAUUGAUU-3' (S)<br>3'-UCCUAAGGAUGUCCUUCGUUCGUUCAUCAUUAACU-5' (AS) | SEQ ID NO:5<br>SEQ ID NO:25 |
| | 21S+10rc | 5'-GGAAGCAAGUAGUAAUUGAUU-3' (S)<br>3'-ACCAGUACGAGUCCUUCGUUCGUUCAUCAUUAACU-5' (AS) | SEQ ID NO:5<br>SEQ ID NO:26 |
| | 16S+10r | 5'-AGCAAGUAGUAAUUGA-3' (S)<br>3'-UCCUAAGGAUGUCCUUCGUUCAUCAUUAACU-5' (AS) | SEQ ID NO:17<br>SEQ ID NO:25 |
| | 16S+10rc | 5'-AGCAAGUAGUAAUUGA-3' (S)<br>3'-ACCAGUACGAGUCCUUCGUUCAUCAUUAACU-5' (AS) | SEQ ID NO:17<br>SEQ ID NO:26 |

FIG. 11

| | | | |
|---|---|---|---|
| CTNNB1-2 | 19+2 | 5'-CUAUCAAGAUGAUGCAGAAUU-3' (S)<br>3'-UUGAUAGUUCUACUACGUCUUAA-5' (AS) | SEQ ID NO:27<br>SEQ ID NO:28 |
| | asiRNA | 5'-UCAAGAUGAUGCAGAA-3' (S)<br>3'-UUGAUAGUUCUACUACGUCUU-5' (AS) | SEQ ID NO:29<br>SEQ ID NO:28 |
| | 16S+15d | 5'-UCAAGAUGAUGCAGAA-3' (S)<br>3'-caacattgaactaattGAUAGUUCUACUACGUCUU-5' (AS) | SEQ ID NO:29<br>SEQ ID NO:30 |
| | 16S+15c | 5'-UCAAGAUGAUGCAGAA-3' (S)<br>3'-ggcaccagtacgaggttGAUAGUUCUACUACGUCUU-5' (AS) | SEQ ID NO:29<br>SEQ ID NO:31 |

FIG. 13

NUCLEIC ACID MOLECULES INDUCING RNA INTERFERENCE, AND USES THEREOF

This application is a continuation of U.S. patent application Ser. No. 15/474,615 filed Mar. 30, 2017 (U.S. Pat. No. 10,214,744), which is a divisional of U.S. patent application Ser. No. 13/880,670 (U.S. Pat. No. 9,637,742), which is a U.S. national phase application under 37 U.S.C. § 371 of International Patent Application No. PCT/KR11/06632, filed Sep. 7, 2011, which claims priority to Korean Patent Application No. 10-2010-0103701, filed Oct. 22, 2010, and Korean Patent Application No. 10-2011-0062504, filed Jun. 27, 2011, the content of each of which is hereby incorporated herein by reference in its entirety.

TECHNICAL FIELD

The present invention relates to an RNAi-inducing nucleic acid molecule having a new structure and the use thereof, and more particularly to a novel nucleic acid molecule having a structure consisting of a first strand, which is 24-121 nucleotides (nt) in length and comprises a partial region complementary to a target nucleic acid, and a second strand which is 13-21 nt in length and has a region that binds complementarily to the partial region complementary to the target nucleic acid within the first strand, so that the nucleic acid molecule inhibits the expression of the target gene with increased efficiency, and to a method of inhibiting the expression of a target gene using the nucleic acid molecule.

BACKGROUND ART

RNA interference (RNAi) is a mechanism capable of inhibiting the expression of a gene in a highly specific and efficient manner, in which degradation of the mRNA of a target gene is induced by introducing a double-stranded RNA, which comprises a sense strand having a sequence homologous to the mRNA of the target gene and an antisense strand having a sequence complementary to the mRNA of the target gene, into cells or the like, thereby inhibiting the expression of the target gene.

In most siRNAs which have been used in the art, the length of the antisense strand is limited to 19-23 nucleotides (nt). This is because the structure of siRNAs which have been used by researchers mimics the structure of products obtained by cutting long dsRNAs in cells by a dicer (El-bashir et al. *Nature* 2001, 411:494-498). In addition, early X-ray crystallography studies suggested a model in which the 5' and 3' ends of the siRNA antisense strand introduced into Argonaute-2 (Ago2) that is the key element of a RISC complex are bound to the mid domain and the binding pocket of the PAZ domain, respectively (Song et al. *Nat. Struct. Biol.* 2003, 10: 1026-1032), but subsequent studies revealed that the 3' end following the 16th nucleotide of the antisense strand is not bound to the PAZ domain (Wang et al. *Nature* 2009, 461: 754-761). This suggests that there can be flexibility in the sequence and length of the 3' end of the siRNA antisense strand.

Meanwhile, an additional study on siRNA reported a modified siRNA-DNA construct, which comprises a single-stranded DNA molecule that can function as a primer for PCR to detect siRNA in a sample (US 2009/0012022 A1). However, the modified siRNA-DNA construct merely has an additional tool for quantification, but has no positive influence on the efficiency with which a target gene is inhibited.

Accordingly, the present inventors have made extensive efforts to a novel, RNAi-inducing nucleic acid molecule which inhibits a target gene with increased efficiency, and as a result, have designed a double-stranded nucleic acid molecule comprising a first strand, which is 24-121 nt in length and comprises a region complementary to a target nucleic acid, and a second strand which is 13-21 nt in length and has a region that binds complementarily to the region of the first strand, which is complementary to the target nucleic acid, and the present inventors have predicted that a nucleic acid oligonucleotide contained in the single-stranded region at the 3' end of the first strand will target other target genes or guide this nucleic acid molecule to the target gene. In addition, the present inventors have constructed a nucleic acid molecule structure, which has a long single-stranded region at the 3' end of the first strand, using an siRNA structure (Korean Patent Laid-Open Publication No. 10-2009-0065880 filled by the present inventors) which shows minimized off-target effects and does not saturate the RNAi machinery, and the present inventors have predicted that a nucleic acid oligonucleotide, which is contained in the single-stranded region at the 3' end of the first strand, can show the effect of targeting other target genes or guiding the siRNA at the 5' end to the target gene, while off-targeting effects will be minimized, thereby completing the present invention.

The above information disclosed in this Background section is only for enhancement of understanding of the background of the present invention, and therefore it may contain information that does not form the prior art that is already known to a person of ordinary skill in the art.

SUMMARY OF INVENTION

It is an object of the present invention to provide a RNAi-inducing nucleic acid molecule having a novel structure and an improved effect on the inhibition of gene expression.

To achieve the above object, the present invention provides an RNAi-inducing nucleic acid molecule comprising a first strand, which is 24-121 nt in length and comprises a region complementary to a target nucleic acid, and a second strand which is 13-21 nt in length and has a region that binds complementarily to the region of the first strand, which is complementary to the target nucleic acid.

The present invention also provides a nucleic acid complex comprising a cell delivery vehicle bound to the RNAi-inducing nucleic acid molecule.

The present invention also provides a method for intracellular delivery of an RNAi-inducing nucleic acid molecule, the method comprising introducing the above nucleic acid complex into a cell.

The present invention also provides a composition for inhibiting gene expression, which contains the above RNAi-inducing nucleic acid molecule.

The present invention also provides a kit for inhibiting gene expression, which contains the above RNAi-inducing nucleic acid molecule.

The present invention also provides a method for inhibiting gene expression, which comprises a step of introducing the above RNAi-inducing nucleic acid molecule into a cell.

The present invention also provides a method for inhibiting expression of a target gene in a cell, the method comprising a step of expressing the above RNAi-inducing nucleic acid molecule in the cell.

The present invention also provides an anticancer composition containing the above RNAi-inducing nucleic acid molecule.

The present invention also provides a method of preventing or treating cancer using the above RNAi-inducing nucleic acid molecule.

Other features and embodiments of the present invention will be more apparent from the following detailed descriptions and the appended claims.

BRIEF DESCRIPTION OF THE DRAWINGS

FIG. 4 shows a structure obtained by extending a target mRNA-targeting ribozyme or DNAzyme sequence at the 3' end of a siRNA structure.

FIG. 5 shows siRNA molecule structures that inhibit the expression of the gene KRAS which is involved in the growth of cancer cells.

FIG. 8 shows asiRNA and lasiRNA molecule structures for KRAS.

FIG. 11 shows lsiRNA (21S+10r) and lasiRNA (16S+10r), which have an extended sequence complementary to mRNA, for KRAS, and molecule structures (21S+10rc and 16S+10rc) having an extended sequence non-complementary to mRNA.

FIG. 13 shows asiRNA and lasiRNA molecule structures for CTNNB1-2.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods which will be described later are those well known and commonly employed in the art.

The definition of main terms used in the detailed description of the invention is as follows.

As used herein, the term "RNAi" (RNA interference) refers to a mechanism by which a double-stranded RNA (dsRNA) consisting of a strand having a complementary to the mRNA of a target gene and a strand having a sequence complementary thereto is introduced into cells or the like to induce the degradation of the mRNA of the target gene to thereby inhibit the expression of the target gene.

As used herein, the term "siRNA" (small interfering RNA) refers to a short double-stranded RNA (dsRNA) that mediates efficient gene silencing in a sequence-specific manner.

As used herein, the term "antisense strand" refers to a polynucleotide that is substantially or 100% complementary to a target nucleic acid of interest. For example, an antisense strand may be complementary, in whole or in part, to a molecule of mRNA (messenger RNA), an RNA sequence that is not mRNA (e.g., microRNA, piwiRNA, tRNA, rRNA and hnRNA) or a sequence of DNA that is either coding or non-coding. The terms "antisense strand" and "guide strand" are used interchangeably herein.

The term "sense strand" refers to a polynucleotide that has the same nucleotide sequence, in whole or in part, as a target nucleic acid, in which the polynucleotide is identical, in whole or in part, a molecule of mRNA (messenger RNA), an RNA sequence that is not mRNA (e.g., microRNA, piwiRNA, tRNA, rRNA and hnRNA) or a sequence of DNA that is either coding or non-coding.

As used herein, the term "gene" is intended to have the broadest meaning, and the gene can encode a structural protein or a regulatory protein. Herein, the regulatory protein includes a transcriptional factor, a heat shock proteins, or a protein that is involved in DNA/RNA replication, transcription and/or translation. Also, the target gene whose expression is to be inhibited is resident in a viral genome which has integrated into the animal gene or may be present as an extrachromosomal element. For example, the target gene may be a gene on an HIV genome. In this case, the genetic construct is useful in inactivating translation of the HIV gene in a mammalian cell.

Figure 1:
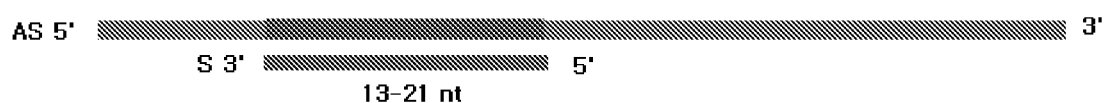
FIG. 1 is a schematic view showing an RNAi-inducing nucleic acid molecule according to the present invention.

In one aspect, the present invention is directed to an RNAi-inducing nucleic acid molecule comprising a first strand, which is 24-121 nt in length and comprises a region complementary to a target nucleic acid, and a second strand which is 13-21 nt in length and has a region that binds complementarily to the region of the first strand, which is complementary to the target nucleic acid (see FIG. 1).

In the present invention, examples of the target nucleic acid include, but are not limited to, mRNA (messenger RNA), microRNA, piRNA (piwi-interacting RNA), a coding DNA sequence and a non-coding DNA sequence.

In the present invention, the region complementary to the target nucleic acid in the first strand is preferably 19-21 nt in length. Thus, the first strand comprises a single-stranded region which does not bind to the second strand. Preferably, the first strand may further comprise, in the single-stranded region, a nucleic acid oligonucleotide selected from the group consisting of antisense DNA, antisense RNA, ribozyme and DNAzyme.

In the present invention, the single-stranded region of the first strand, which does not bind complementarily to the second strand, can be linked directly or by a linker to the region that binds complementarily to the second strand. Herein, the linker may be a chemical linker. Examples of the chemical linker include, but are not limited to, a nucleic acid moiety, PNA (a PNA moiety), a peptide moiety, a disulfide bond or a polyethylene glycol moiety.

In the present invention, the first strand may further comprise, in the single-stranded region, a sequence that is complementary or non-complementary to the target nucleic acid. When the first strand comprises the complementary sequence, the complementary sequence may be located consecutively from the double-stranded region of the nucleic acid molecule of the present invention, that is, the region of siRNA, which is complementary to the target nucleic acid. Alternatively, the complementary sequence may also be located apart from the double-stranded region. Likewise, the sequence that is targeted by siRNA, and the sequence that is targeted by the ribozyme or DNAzyme of the single-stranded region may be located consecutively or located apart from each other. In addition, in the case in which the single-stranded region of the first strand has the sequence complementary to the target gene targeted by the siRNA, when the sequence contained in the single-stranded region is antisense DNA or antisense RNA, the sequence may be at least about 70-80%, more preferably at least about 80-90%, and even more preferably at least 95-99% complementary to the sequence of the target gene targeted by the siRNA, and when the single-stranded region is ribozyme or DNAzyme, the sequence of the single-stranded region may be at least about 50-60% complementary to the sequence of the target gene targeted by the siRNA.

In addition, the single-stranded region may be 5-100 nt in length. If the length of the single-stranded region is less than 5 nt, the effect of increasing the efficiency with which gene expression is inhibited will be insignificant, and if the length is more than 100 nt, the efficiency with which an RNA molecule is synthesized will be reduced. Preferably, the single-stranded region may be 9-100 nt in length or 50 nt or less in length. More preferably, the single-stranded region may be 10-15 nt in length.

In the present invention, at least one of the nucleotides of the single-stranded region in the first strand may comprise a bulky base analog. When an extended sequence comprises a bulky base analog such as a deoxyadenosine derivative having a phenyl group, a mRNA strand that binds complementarily to the extended sequence is cleaved at the location of the bulky base analog. Any bulky base analog that induces this cleavage may be used without limitation in the present invention.

In the present invention, it was predicted that the 5' end of a nucleic structure obtained by extending the antisense strand of siRNA in a manner complementary to a target mRNA sequence will function as the RNAi mechanism while the 3' end will function as an antisense mechanism or guide the 5' end siRNA to the target mRNA. When the sequence of the antisense 3'-end, which is complementary to mRNA, is DNA, it can induce RNase H-dependent mRNA cleavage. In addition, it was predicted that when at least one of the nucleotides of the single-stranded region of the antisense 3'-end comprises a bulky base analog or the single-stranded region binds to mRNA to form a bulge structure, cleavage can be induced. Further, when a nucleic acid molecule comprising the ribozyme or DNAzyme introduced into the single-stranded region of the first strand can induce synergistic cleavage.

Korean Patent Laid-Open Publication No. 10-2009-0065880 discloses an siRNA structure which is an siRNA molecule consisting of a 19-21 nt antisense strand and a 13-16 nt sense strand, in which the 5' end of the antisense strand is a blunt end. This siRNA structure inhibits gene expression at high efficiency without causing off-target effects by the sense strand of siRNA or inhibiting other RNAi mechanisms. When the structure of the present invention is applied to this siRNA, off-target effects can be minimized while the above-described effect of the nucleic acid oligonucleotide contained in the single-stranded region of the first strand can be obtained. As used herein, the term "off-target effects" refers to any instance in which the sense strand of siRNA causes the unexpected degradation of other mRNAs or the silencing of the corresponding genes, and the antisense strand of siRNA is paired with undesired targets to cause the degradation of other mRNAs or the silencing of the corresponding genes, even though siRNA is originally used to induce degradation of mRNA having a sequence complementary to the antisense strand so as to obtain the effect of inhibiting the gene expression of the mRNA.

The siRNA molecule of the present invention may be a molecule synthesized according to a general method, but is not limited thereto. In other words, in the present invention, the siRNA molecule may chemically or enzymatically synthesized. The siRNA molecule of the present invention may be derived from naturally occurring genes by standard recombinant techniques. In this case, the siRNA molecule may be substantially complementary at the nucleotide sequence level to at least a portion of mRNA of the target gene, the expression of which is to be changed.

Accordingly, the nucleic acid molecule of the present invention may comprise a chemical modification. The chemical modification may be obtained by replacing the hydroxyl group at position 2' of ribose of at least one nucleotide, included in the nucleic acid molecule, by any one of a hydrogen atom, a fluorine atom, an —O-alkyl group, an —O-acyl group and an amino group, but is not limited thereto. In order to increase the ability to deliver the nucleic acid molecule, the hydroxyl group may be replaced by any one of —Br, —Cl, —R, —R'OR, —SH, —SR, —N$_3$ and —CN (R=alkyl, aryl, or alkylene). In addition, the chemical modification may be obtained by replacing the phosphate backbone of at least one nucleotide by any one of a phosphorothioate form, phosphorodithioate form, alkylphosphonate form, phosphoroamidate form and boranophosphate form. Further, the chemical modification may be obtained by replacing at least one nucleotide included in the nucleic acid molecule by any one of LNA (locked nucleic acid), UNA (unlocked nucleic acid), morpholino and PNA (peptide nucleic acid). In addition, the chemical modification may be obtained by binding the nucleic acid molecule to one or more selected from the group consisting of lipids, cell penetrating peptides and cell targeting ligands.

In addition, the nucleic acid molecule according to the present invention may be bound to a cell delivery vehicle for introduction into a cell. Thus, in another aspect, the present invention is directed to a nucleic acid complex comprising a cell delivery vehicle bound to the RNAi-inducing nucleic acid molecule.

In the present invention, the cell delivery vehicle may be selected from the group consisting of cationic polymers, lipids, cell penetrating peptides and cell targeting ligands. Cationic cell delivery vehicles such as cationic polymers and cationic lipids are positively charged reagents that are used to deliver nucleic acid (i.e., siRNA) into cells in vitro or in vivo. The cationic cell delivery vehicle can strongly interact with the nucleic acid molecule of the present invention to form a complex so that the RNAi-inducing nucleic acid molecule can be effectively introduced into a cell. The cell delivery vehicle that is used in the present invention may be a cationic polymer such as polyethyleneimine (PEI) or a liposome such as Lipofectamine 2000 (Invitrogen), but is not limited thereto. It will be obvious to those skilled in the art that a positively charged reagent can be used to provide the complex according to the present invention. Further, a lipid such as cholesterol may be linked directly to the nucleic acid molecule or linked indirectly to the nucleic acid molecule through another cell delivery vehicle.

In addition, embodiments of the present invention suggest that the RNAi-inducing nucleic acid molecule of the present invention provides the effect of efficiently inhibiting the expression of a target gene. Thus, in still another aspect, the present invention is directed to a composition for inhibiting gene expression, which contains the above RNAi-inducing nucleic acid molecule. Herein, the nucleic acid molecule may be in the form of a nucleic acid complex having the cell delivery vehicle bound thereto.

In an example of the present invention, it was found that, when the nucleic acid structure of the present invention was applied to an siRNA targeting the target gene KRAS or CTNNB1-2, the efficiency with which the expression of the target gene is inhibited could be significantly increased, and the efficacy thereof could also be maintained for a long period of time. Thus, it will be obvious to those skilled in the art that, even when nucleic acid molecules targeting other target genes are provided according to the present invention, the same results can be obtained.

Meanwhile, the composition for inhibiting gene expression according to the present invention may be provided in the form of a kit for inhibiting gene expression. The kit for inhibiting gene expression may take the form of bottles, tubs, sachets, envelops, tubes, ampoules, and the like, which may be formed in part or in whole from plastic, glass, paper, foil, wax, and the like. The container may be equipped with a fully or partially detachable lid that may initially be part of the container or may be affixed to the container by mechanical, adhesive, or other means. The container may also be equipped with a stopper, allowing access to the contents by a syringe needle. The kit may comprise an exterior package which may include instructions regarding the use of the components.

In yet another aspect, the present invention is directed to a method of inhibiting expression of a target gene in a cell using the above RNAi-inducing nucleic acid molecule. That is, the present invention is directed to a method for inhibiting expression of a target gene in a cell, which comprises a step of introducing the above RNAi-inducing nucleic acid molecule into a cell.

In the present invention, the first strand of the RNAi-inducing nucleic acid may be complementary to the mRNA sequence of a target gene.

In the present invention, the target gene may be an endogeneous gene or a transgene.

The nucleic acid molecule according to the present invention is not necessarily limited to a synthetic siRNA and can also advantageously be applied to siRNA or shRNA, which is expressed in cells using an expression vector or the like. In other words, the nucleic acid molecule of the present invention can be expressed in cells to inhibit the expression of the target gene. Thus, in a further aspect, the present invention is directed to a method for inhibiting expression of a target gene in a cell, the method comprising a step of expressing the above RNAi-inducing nucleic acid molecule in the cell.

Meanwhile, the RNAi-inducing nucleic acid molecule of the present invention can be used to inhibit the expression of the target gene such as a gene that causes or grows cancer by over-expression, that is, a tumor-related gene. Thus, the RNAi-inducing nucleic acid molecule is useful as an anti-cancer composition. Herein, the tumor-related gene may be any one of KRas, Wnt-1, Hec1, Survivin, Livin, Bcl-2, XIAP, Mdm2, EGF, EGFR, VEGF, VEGFR, Mcl-1, IGF1R, Akt1, Grp78, STAT3, STAT5a, β-catenin, WISP1 and c-myc, but is not limited thereto. In one example of the present invention, it was found that the gene KRAS involved in the growth of cancer cells was inhibited by introducing the siRNA molecule of the present invention into cells. In addition, it was shown that an siRNA molecule targeting the beta-catenin gene killed a cancer cell line.

The anticancer composition of the present invention may be provided as a pharmaceutical composition comprising the RNAi-inducing nucleic acid molecule or a complex comprising the nucleic acid molecule bound to a cell delivery vehicle alone or in combination with at least one pharmaceutically acceptable carrier, excipient or diluent. The complex may be contained in the pharmaceutical composition in a pharmaceutically effective amount according to a disease and the severity thereof, the patient's age, weight, health condition and sex, the route of administration and the period of treatment.

As used herein, the term "pharmaceutically acceptable composition" refers to a composition that is physiologically acceptable and does not cause gastric disorder, allergic reactions such as gastrointestinal disorder or vertigo, or similar reactions, when administered to humans. Examples of said carrier, excipient or diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methylhydroxybenzoate, propylhydroxybenzoate, magnesium stearate and mineral oils.

The pharmaceutical composition may additionally contain fillers, anti-aggregating agents, lubricants, wetting agents, perfumes, emulsifiers and preservatives. Also, the pharmaceutical composition of the present invention may be formulated using a method well known in the art, such that it can provide the rapid, sustained or delayed release of the active ingredient after administration to mammals. The formulation may be in the form of sterile injection solutions, etc.

Meanwhile, the RNAi-inducing nucleic acid molecule of the present invention or a complex comprising the nucleic acid molecule bound to a cell delivery vehicle may further comprise a known anticancer chemotherapeutic agent to provide combined effects. Examples of a known anticancer chemotherapeutic agent that may be used in the present invention include cisplatin, carboplatin, oxaliplatin, doxorubicin, daunorubicin, epirubicin, idarubicin, mitoxantrone, valubicin, curcumin, gefitinib, erlotinib, irinotecan, topotecan, vinblastine, vincristine, docetaxel, paclitaxel and the like.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Construction of Long-Antisense-Guided siRNA: Preparation Example 1

Figure 2:
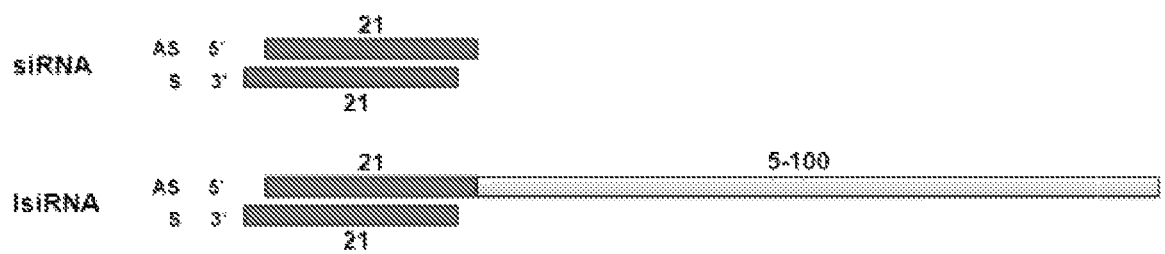
FIG. 2 shows a long-antisense siRNA (lsiRNA) obtained by extending the 3' end of the antisense strand to provide a sequence complementary to a target mRNA.

An siRNA was constructed in the following manner: the second strand had a short length of 21 nt; the region of the first strand, which forms a double strand with the second strand, was 19 nt in length; and the 3' end of the first strand had a 17-nt single-stranded region complementary to a target mRNA. The constructed siRNA having the long antisense strand was named "long-antisense siRNA (lsiRNA)". The nucleic acid oligonucleotide included in the extended sequence allows the siRNA to be guided to the target mRNA or to function as a typical antisense mechanism (see FIG. 2).

Example 2: Construction of Long-Antisense asiRNA: Preparation Example 2

Figure 3:
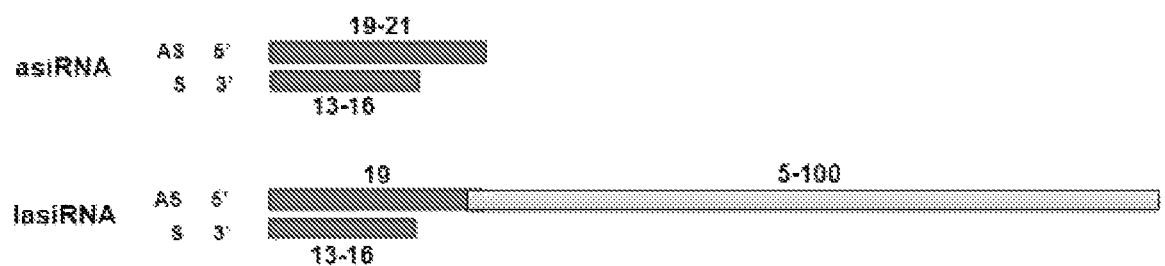
FIG. 3 shows a long-antisense asiRNA (lasiRNA) obtained by extending the 3' end of the antisense strand of an asiRNA structure to provide a sequence complementary to a target mRNA.

An siRNA was constructed in the following manner: the second strand had a short length of 15 nt; the region of the first strand, which forms a double strand with the second strand, was 19 nt in length; the 3' end of the first strand had a 17-nt extended sequence complementary to a target mRNA; and the 5' end of the first strand was a blunt end. The constructed siRNA having the long antisense strand was named "long-antisense asiRNA (lasiRNA)". The nucleic acid oligonucleotide included in the extended sequence allows the siRNA to be guided to the target mRNA or to function as a typical antisense mechanism (see FIG. 3).

Example 3: Construction of DNAzyme (or Ribozyme)-Guided siRNA (siRZNA): Preparation Example 3

A structure having a long antisense strand was constructed using CTNNB1-2siRNA and Dz339 DNAzyme in the following manner: the sense strand had a short length of 21 nt; and the 3' end of the 19-nt antisense strand had DNAzyme. The constructed structure was named "DNAzyme-guided siRNA (siRZNA)" (see FIG. 4).

Example 4: Construction of lsiRNA that Inhibits Expression of KRAS Gene and Examination of the Ability to Inhibit Expression of KRAS Gene An siRNA that inhibits the expression of the gene KRAS involved in the growth of cancer cells was designed. In addition, long antisense siRNAs (lsiRNAs) were constructed by adding each of 5 nt, 10 nt and 15 nt to the 3' end of the antisense strand of a conventional siRNA structure (19+2). Herein, structures (21S+5d, 10d and 15d) having an extended DNA sequence complementary to a target mRNA, and control structures (21S+5c, 10c and 15c) having an extended DNA sequence non-complementary to a target mRNA were constructed, and the efficiencies with which the constructed structures inhibit the expression of the target gene were compared with each other (see FIG. 5). In addition, a structure (21+15d-mut) was constructed by mutating the seed sequence of lsiRNA, and whether the ability of lsiRNA to inhibit gene expression is dependent on the seed sequence, like siRNA, was tested. Each of siRNA and lsiRNA was transfected into AGS cells (ATCC CRL 1739, Gastric adenocarcinoma, human) at a concentration of 10 nM using lipofectamine 2000 (Invitrogen). Primers used in real-time PCR for mRNA measurement are as follows:

```
KRAS
forward sequence
                                (SEQ ID NO: 15)
5'-GAGTGCCTTGACGATACAGC-3';
and
```

-continued

```
reverse sequence
                                (SEQ ID NO: 16)
5'-CCCTCATTGCACTGTACTCC-3'.
```

Figure 6:
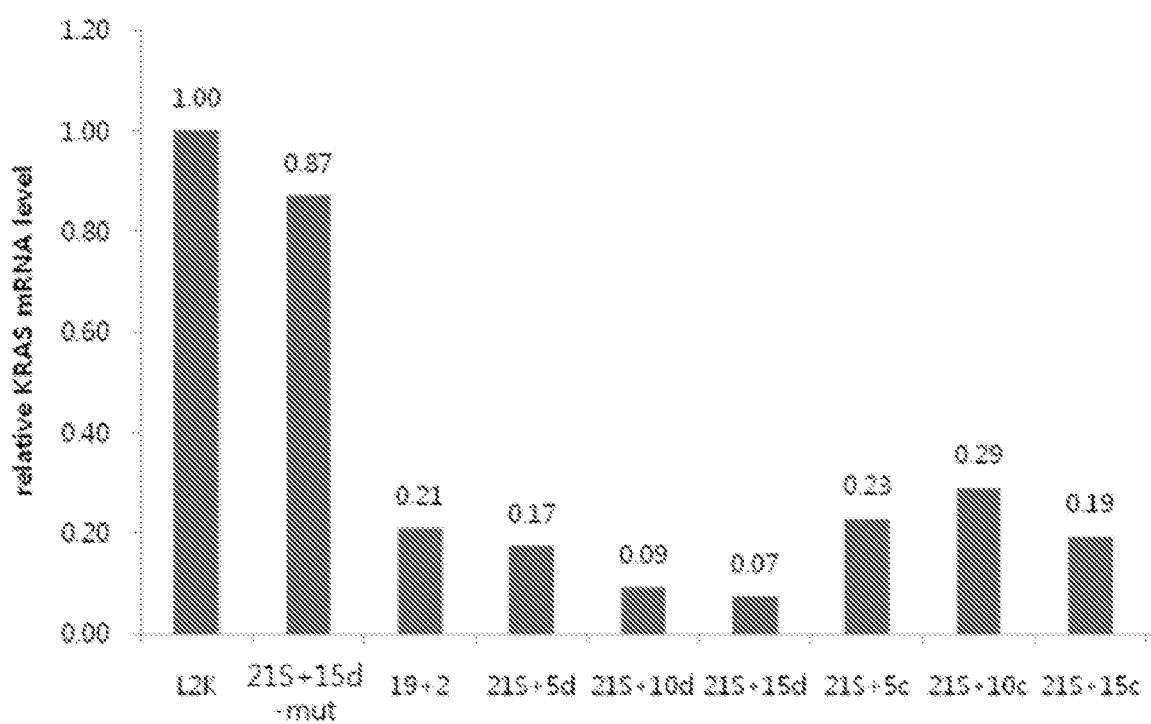
FIG. 6 is a graphic diagram showing relative KRAS mRNA levels caused by introduction of nucleic acid molecules shown in FIG. 5.

As a result, as can be seen in FIG. 6, the lsiRNA having the single-stranded region complementary to the target mRNA showed an improved ability to inhibit the target gene, compared to the conventional siRNA structure, and this tendency was proportional to the length of the single-stranded region. However, in the case of the control lsiRNA having the single-stranded region non-complementary to the target mRNA, this improved ability to inhibit gene expression could not be observed. In the case of the lsiRNA having the seed sequence mutation, the ability to inhibit the target gene nearly disappeared. This suggests that lsiRNA inhibits the target gene by the seed sequence-dependent RNAi mechanism, like conventional siRNA, and does not show nonspecific gene silencing caused by the modified structure.

Figure 7:
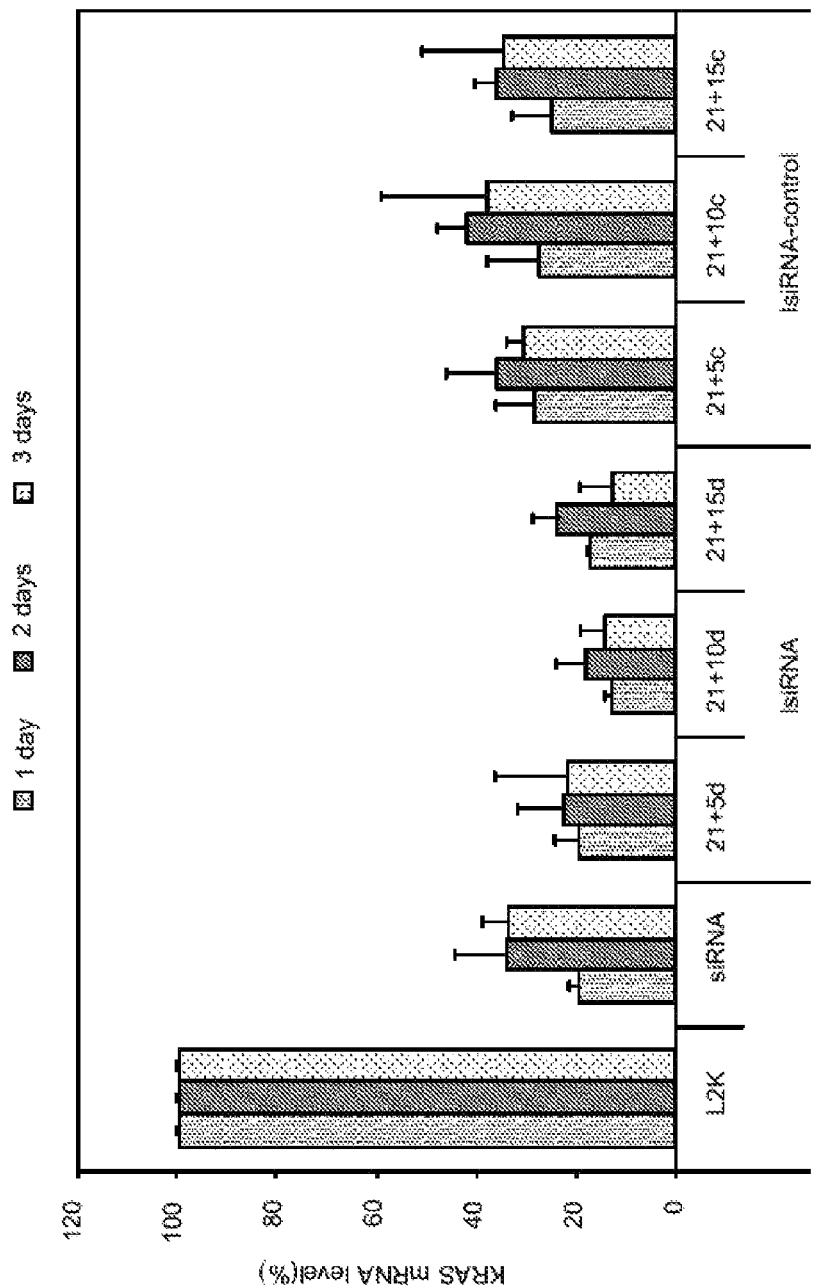
FIG. 7 is a graphic diagram showing the results of measuring KRAS mRNA expression levels, caused by introduction of nucleic acid molecules shown in FIG. 5, at day 1, day 2 and day 3.

Then, whether the ability of lsiRNA to inhibit the target gene is sufficiently maintained after intracellular introduction compared to that of siRNA was examined. It was shown that the ability of the conventional siRNA structure to inhibit gene expression reached a maximum at 1 day after intracellular introduction and reduced at 2 days and 3 days after intracellular introduction (see FIG. 7). However, the ability of lsiRNA to inhibit the expression of the target gene was maintained even up to 3 days after intracellular introduction. On the contrary, in the case of the control lsiRNA having the single-stranded region non-complementary to the target mRNA, this improved ability to inhibit gene expression could not be observed. Such results suggest that the lsiRNA having the single-stranded region complementary to the mRNA of the target gene exhibits the high efficiency with which it inhibits gene expression, compared to the conventional siRNA structure, and the efficacy thereof is also maintained for a longer period of time.

Example 5: Construction of lasiRNA that Inhibits Expression of KRAS Gene and Examination of the Ability to Inhibit Expression of KRAS Gene In addition to Example 4, examination was performed in order to determine whether the nucleic acid molecule structure of the present invention, when applied to an asymmetric shorter duplex siRNA (asiRNA), can improve the ability to inhibit the expression of the target gene.

Figure 9:
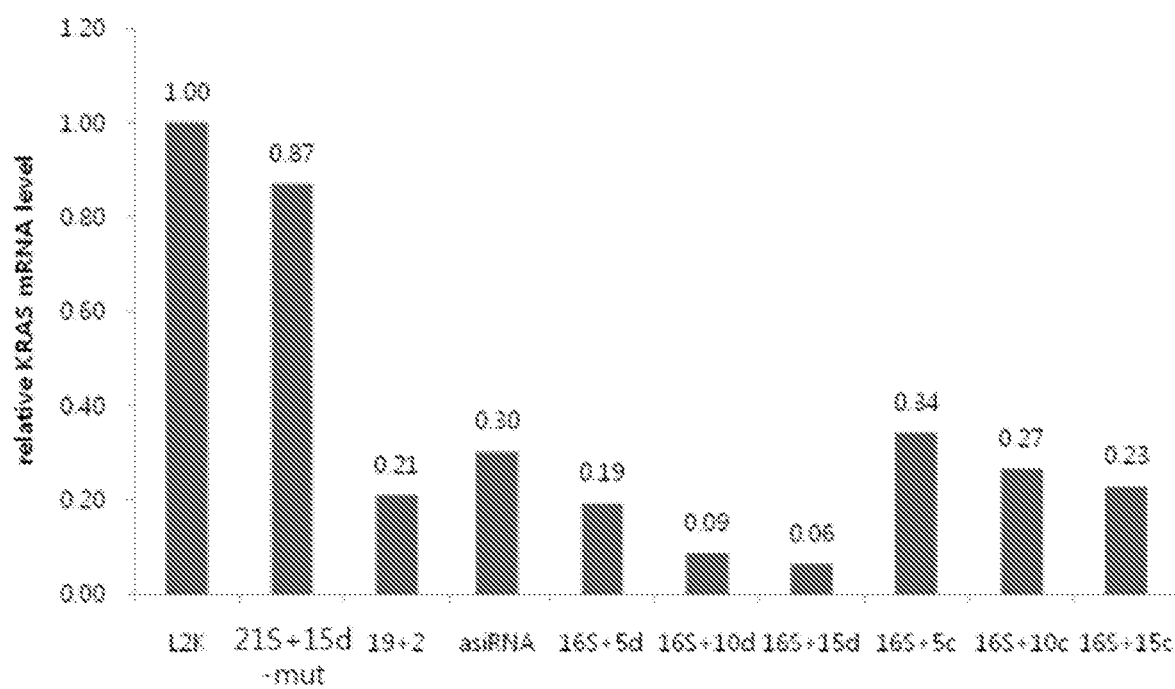
FIG. 9 is a graphic diagram showing relative KRAS mRNA levels caused by introduction of the nucleic acid molecules shown in FIG. 8.

In a manner similar to Example 4, structures (16S+5d, 10d and 15d) were constructed by extending the 3' end of the antisense strand of the conventional asiRNA structure with DNA having a sequence complementary to a target mRNA, and control structures (16S+5c, 10c and 15c; long antisense asiRNA (lasiRNA)) having an extended DNA sequence non-complementary to a target mRNA were constructed (see FIG. 8). The constructed structures were transfected into AGS cells, and the abilities to inhibit the growth of cancer cells were compared. These RNAs were transfected into AGS cells, and then real-time PCR was performed in the same manner as described in Example 4 in order to verify the efficiencies with which the structures inhibit the expression of the target gene KRAS (see FIG. 9). Each of asiRNA and lasiRNA was transfected into AGS cells (ATCC CRL 1739, Gastric adenocarcinoma, human) at a concentration of 10 nM using lipofectamine 2000 (Invitrogen).

As a result, the target mRNA inhibitory ability of the lasiRNA having the extended single-stranded sequence complementary to the target mRNA increased in proportional to the length of the extended sequence, similar to the case of lsiRNA. However, this effect was not observed in the case in which the extended sequence was not complementary to the target mRNA.

Example 6: lasiRNA that Inhibits Expression of KRAS Gene and Examination of the Ability of lasiRNA to Inhibit Growth of AGS Cancer Cells Then, examination was performed in order to determine whether the KRAS-targeting lsiRNA and lasiRNA structures showing an improved ability to inhibit the target gene, compared to siRNA and asiRNA, also have increased ability to inhibit the growth of AGS cancer cells. Specifically, AGS cells seeded in a 96-well plate were transfected with 10 nM of RNA using lipofectamine 2000, and after 5 days, the viability of the cells was measured by visually counting the number of the cells through microscopic observation.

Figure 10:
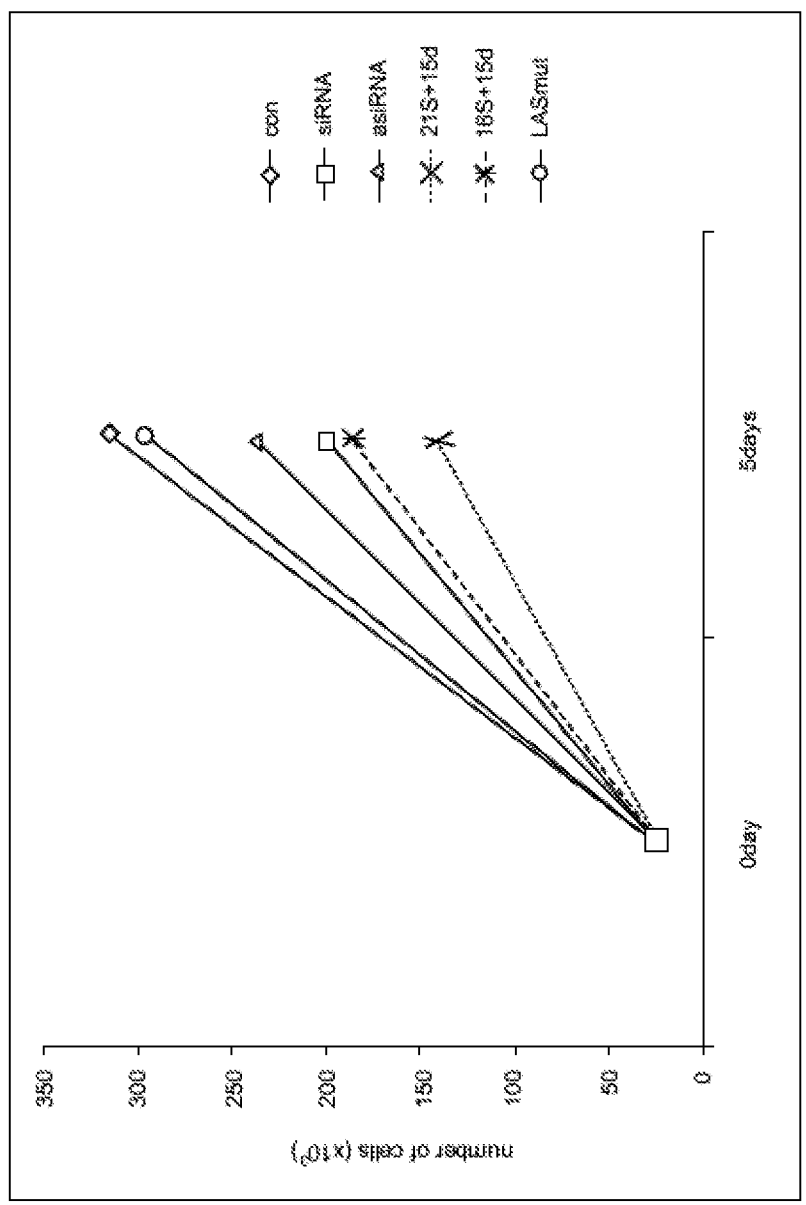
FIG. 10 is a graphic diagram showing the results of measuring the viabilities of an AGS cell line, caused by introduction of the nucleic acid molecules shown in FIG. 8, at day 5.

As a result, it was shown that the ability to inhibit the expression of KRAS mRNA had a high relationship with the ability to inhibit the growth of cancer cells. Specifically, it was shown that lsiRNA (21S+15d) having the extended sequence of 15 nucleotides showed a strong ability to inhibit the growth of cancer cells, compared to siRNA, and the ability of lasiRNA (16S+15d) to inhibit the growth of cancer cells increased compared to that of asiRNA (see FIG. 10). Meanwhile, the lsiRNA having a mutation introduced into the seed sequence (LASmut) did not induce the inhibition of cancer cell growth, suggesting that nonspecific cytotoxicity by the long extended sequence structure does not appear. Such results suggest that, when a single-stranded region complementary to a target mRNA is introduced into the 3' end of the antisense strand of each of siRNA and asiRNA, the ability to inhibit gene expression and the expression of phenotypes in cells can be increased.

Example 7: Examination of the Abilities of lsiRNA and lasiRNA (Having RNA as Extended Sequence) to Inhibit Expression of KRAS Gene Then, examination was performed in order to determine whether the abilities of lsiRNA and lasiRNA (each having RNA in place of DNA as an extended sequence) to inhibit the expression of a target gene increase compared to those of siRNA and asiRNA, which correspond thereto.

As shown in FIG. 11, lsiRNA (21S+10r) and lasiRNA (16S+10r), each having a 10-nt extended sequence complementary to mRNA, were constructed, and control structures (21S+10rc, and 16S+10rc), each having an extended sequence non-complementary to mRNA, were also constructed. The constructed structures were transfected into AGS cells, and then the efficiencies with which they inhibited the expression of KRAS mRNA were examined in the same manner as described in Example 4.

Figure 12:
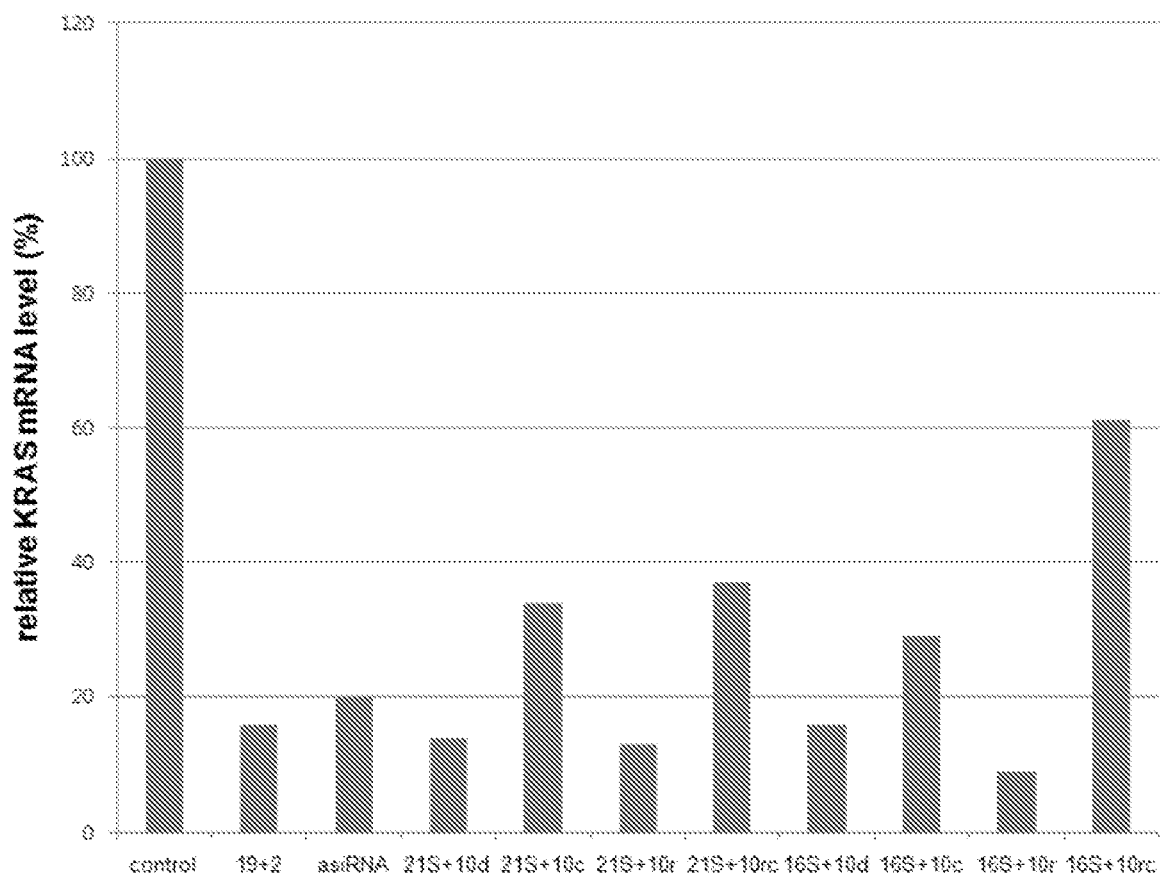
FIG. 12 shows relative KRAS mRNA levels caused by introduction of the nucleic acid molecules shown in FIG. 11.

As a result, as can be seen in FIG. 12, lsiRNA and lasiRNA, which have the extended RNA sequence, had a high ability to inhibit the expression of the target gene, compared to siRNA and asiRNA, which correspond thereto. Particularly, lasiRNA having an extended RNA sequence showed an increased inhibitory ability compared to lasiRNA having an extended DNA sequence. This suggests that the ability to inhibit the expression of the target gene can be achieved even when the long antisense sequence is RNA in addition to DNA.

Example 8: Construction of lasiRNA that Inhibits Expression of CTNNB1 Gene and Examination of the Ability to Inhibit Expression of CTNNB1 Gene 8-1: Measurement of CTNNB1 mRNA Expression Level Then, in order to examine whether the nucleic acid molecule structure of the present invention can increase the activity of asiRNAs that target other genes, lasiRNA structures corresponding asiRNAs targeting beta-catenin (CTNNB1) were constructed (see FIG. 13). Then, each of the constructed structures was transfected into Hep3B cells (ATCC HB 8064) at a concentration of 10 nM using lipofectamine 2000, and then the ability to inhibit the expression of the target gene was examined by real-time PCR.

```
CTNNB1
forward sequence
                                (SEQ ID NO: 32)
5'-ATGTCCAGCGTTTGGCTGAA-3';
and reverse sequence
                                (SEQ ID NO: 33)
5'-TGGTCCTCGTCATTTAGCAGTT-3'.
```

Figure 14:
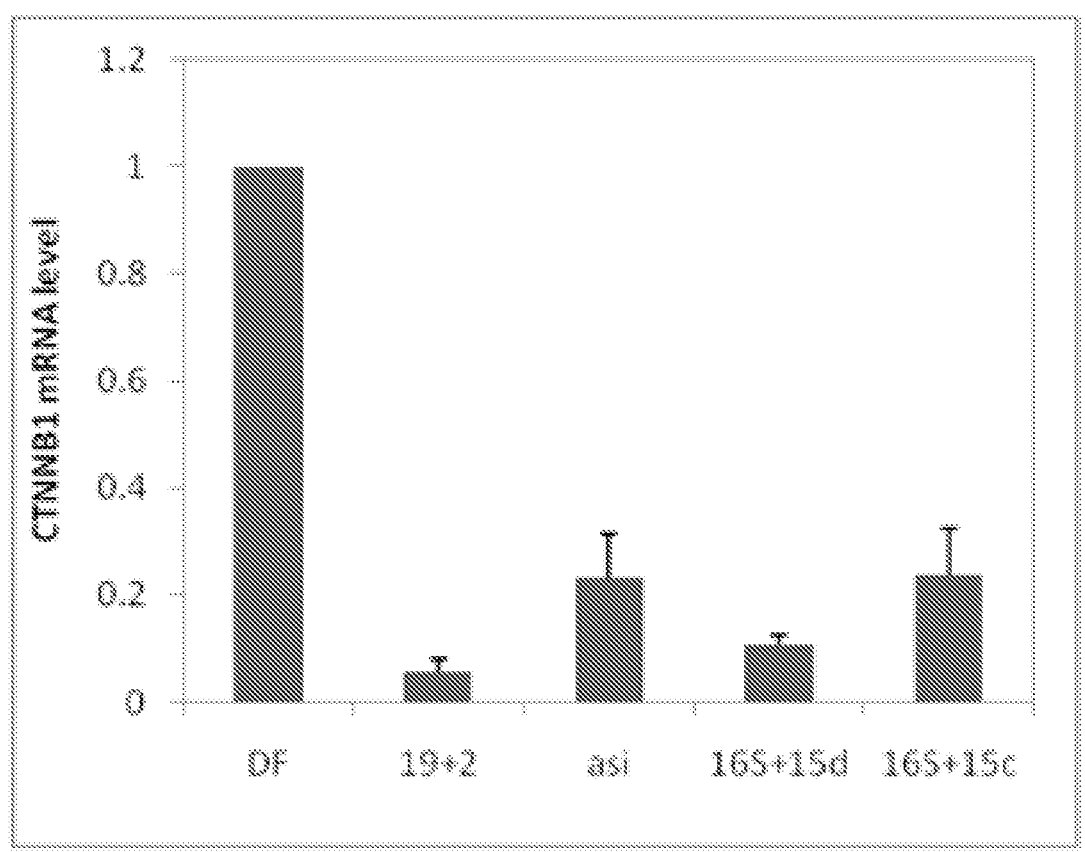
FIG. 14 shows KRAS mRNA expression levels caused by introduction of the nucleic acid molecules shown in FIG. 13.

As a result, as can be seen in FIG. 14, the ability of asiRNA to inhibit the expression of the target gene decreased compared to that of the conventional siRNA structure, but the target gene inhibitory ability of the lasiRNA (16S+15d) having a 15 nt DNA sequence complementary to the mRNA sequence at the 3' end of the antisense strand increased to a level similar to that of siRNA. On the other hand, in the case of the structure (16S+15c) having an extended DNA sequence non-complementary to the target gene, the decrease in the ability to inhibit the target gene was insignificant compared to that of asiRNA. Thus, it was found that the lasiRNA structure has an increased ability to inhibit the target gene, regardless of the asiRNA sequence.

8-2: Measurement of the Ability to Inhibit Growth of Hep3B Cancer Cells

The increased ability of the lasiRNA structure to inhibit the target gene was verified again by measuring the ability to inhibit the growth of Hep3B cancer cells. Specifically, 10 nM of each of siRNA, asiRNA and lasiRNA was transfected into Hep3B cells, and after 5 days, the degree of cell growth was examined by counting the number of the cells. The viability of the cells was examined by visually counting the number of the cells through microscopic observation. Briefly, AGS cells seeded in a 96-well plate were transfected with 10 nM of each of siRNA, asiRNA and lasiRNA, and after 5 days, the number of viable cells was visually counted.

Figure 15:
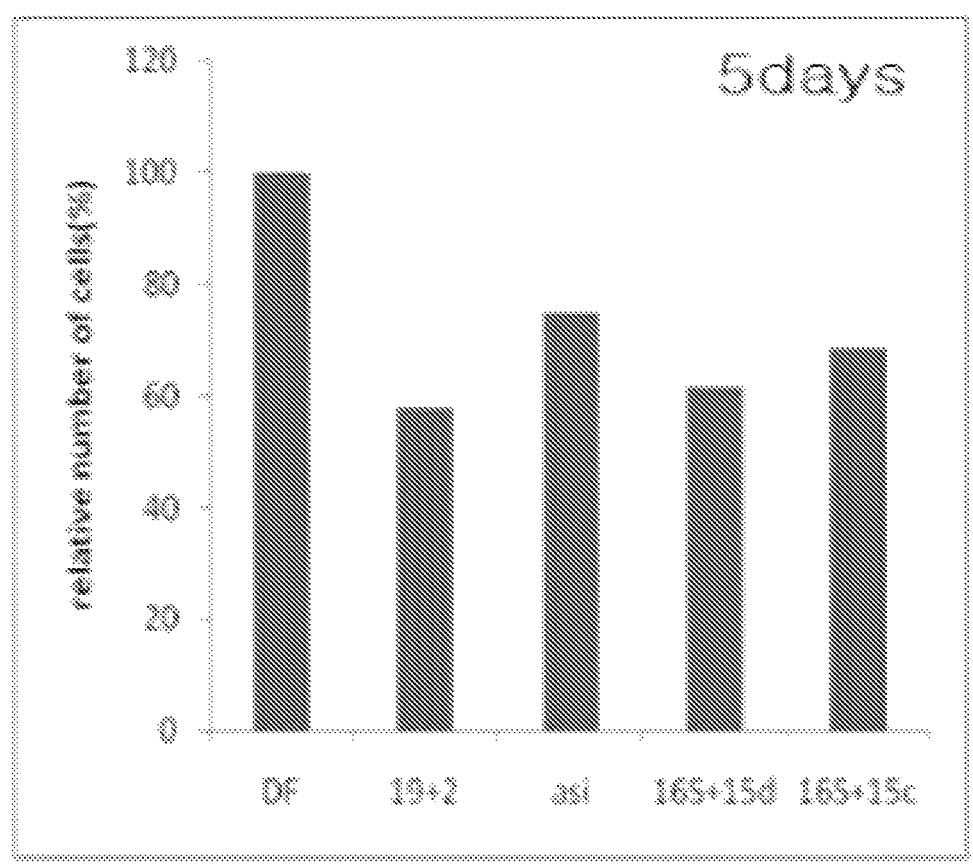
FIG. 15 is a graphic diagram showing the results of measuring the viabilities of a Hep3B cell line, caused by introduction of the nucleic acid molecules shown in FIG. 13, at day 5.

As a result, as can be seen in FIG. 15, the ability of asiRNA to kill cancer cells decreased compared to that of siRNA, but lasiRNA having an extended sequence complementary to the target gene showed cell killing ability similar to that of siRNA. On the other hand, the cell killing ability of lasiRNA having an extended sequence non-complementary to the target gene did not increased compared to that of asiRNA. This suggests that the siRNA molecule containing an extended sequence complementary to the target gene at the 3' end of the antisense strand has an increased ability to inhibit the expression of the target gene.

Example 9: Analysis of Mechanism of Inhibition of Gene Expression

In order to examine whether the nucleic acid molecule of the present invention inhibits gene expression according to the same RNAi mechanism as the conventional 19+2 siRNA or asiRNA, the following test was performed. Specifically, to analyze a cleavage site for a target mRNA, 5'RACE (rapid amplification of cDNA ends) analysis was performed.

First, each of siKRAS, asiKRAS, LaiKRAS and LasiKRAS, constructed in Examples 4 and 5, was introduced into HeLa cells using PEI, and after 18 hours, total RNA was extracted using a Tri-reagent kit (Ambion). The total RNA (3 µg) was ligated with 0.25 µg of GeneRacer RNA oligo, and the GeneRacer RNA oligo-ligated total RNA was reverse-transcribed using GeneRacer oligo dT and SuperScript™ III RT kit (Invitrogen). The RNA oligo-ligated mRNA was amplified using gene-specific primers. The PCR product was cloned into a T&A vector (RBC), and then sequenced with a M13 forward primer.

```
KRAS Gene specific Primer:
                                (SEQ ID NO: 34)
5'-CTGCATGCACCAAAAACCCCAAGACA-3';

KRAS Gene Specific Primer Nested:
                                (SEQ ID NO: 35)
5'-CACAAAGAAAGCCCTCCCCAGTCCTCA-3'.
```

Figure 16:
FIG. 16 is a photograph showing the results of 5'RACE (rapid amplification of cDNA ends) analysis.

As a result, as can be seen in FIG. 16, the cases of treatment with siKRAS, asiKRAS, LsiKRAS and LasiKRAS could provide RACE products having the same size. Also, these RACE products were cloned into T-vectors (RBC), and an accurate cleavage position in the nucleotide sequence was examined by sequencing. As a result, it was shown that, in the cases of siKRAS, asiKRAS, LsiKRAS and LasiKRAS, the mRNA position corresponding to the position between $10^{th}$ nucleotide and $11^{th}$ nucleotide from the 5' end of the antisense was cleaved.

INDUSTRIAL APPLICABILITY

As described above, the nucleic acid molecule structure of the present invention targets a target gene complementary to a portion of the first strand by the nucleic oligonucleotide included in the single-stranded region at the 3' end of the first strand to guide the siRNA into the target gene to thereby increase the efficiency with which the nucleic acid molecule inhibits the target gene. Alternatively, the nucleic acid molecule of the present invention can either increase the ability of the siRNA to bind to the target gene or cause synergistic cleavage, by introduction of antisense DNA, antisense RNA, ribozyme or DNAzyme, thereby increasing the efficiency with which the nucleic acid molecule inhibits the target gene. In addition, when the nucleic acid molecule according to the present invention is used, the efficiency with which the target gene is inhibited can be maintained for an extended period of time. Accordingly, the RNAi-inducing nucleic acid molecule of the present invention can be effectively used for the treatment of cancer or viral infection in place of conventional siRNA molecules.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A long antisense siRNA (lasiRNA) molecule comprising:

a first nucleic acid strand of 26-31 nucleotides (nt) in length and that is 100% complementary to a target nucleic acid; and a second nucleic acid strand of 16 nt in length that binds complementarily to the first nucleic acid strand, such that the first nucleic acid strand has a double-stranded region of 16 nt in length to which the second nucleic acid strand binds and a single-stranded region of 10 nt to 15 nt in length to which the second nucleic acid strand does not bind, and wherein the 5' end of the first nucleic acid strand and the 3' end of the second nucleic acid strand form a blunt end.

2. The lasiRNA molecule of claim 1, wherein the first nucleic acid strand is of 31 nt in length.

3. The lasiRNA molecule of claim 1, wherein the target nucleic acid is a messenger RNA (mRNA).

4. The lasiRNA molecule of claim 1, wherein the lasiRNA molecule comprises a chemical modification.

5. The lasiRNA molecule of claim 4, wherein the chemical modification comprises a replacement of the hydroxyl group at position 2' of ribose of at least one nucleotide included in the lasiRNA molecule by any one of a hydrogen atom, a fluorine atom, an —O-alkyl group, and an amino group.

6. The lasiRNA molecule of claim 4, wherein the chemical modification comprises a replacement of the phosphate backbone of at least one nucleotide included in the lasiRNA molecule by any one of a phosphorothioate form, phosphorodithioate form, alkylphosphonate form, phosphoroamidate form, and boranophosphate form.

7. The lasiRNA molecule of claim 4, wherein the chemical modification comprises a replacement of at least one nucleotide included in the lasiRNA molecule by any one of LNA (locked nucleic acid), UNS (unlocked nucleic acid) morpholino, and PNA (peptide nucleic acid).

8. The lasiRNA molecule of claim 4, wherein the chemical modification comprises a lipid, cell penetrating peptide, or cell-targeting ligand bound to the lasiRNA molecule.

9. The lasiRNA molecule of claim 1, wherein a cell delivery vehicle is bound to the lasiRNA molecule.

10. The lasiRNA molecule of claim 9, wherein the cell delivery vehicle is selected from cationic polymers, lipids, cell penetrating peptides, and cell-targeting ligands.

11. The lasiRNA molecule of claim 1, wherein the target gene is a tumor-related gene.

12. The lasiRNA molecule of claim 11, wherein the tumor-related gene is any one of KRAS, Wnt-1, Hec1, Survivin, Livin, Bcl-2, XIAP, Mdm2, EGF, EGFR, VEGF, VEGFR, Mcl-1, IGF1R, Akt1, Grp78, STAT3, STAT5a, β-catenin, WISP1, and c-myc.

13. The lasiRNA molecule of claim 2, wherein the lasiRNA molecule comprises a chemical modification.

14. The lasiRNA molecule of claim 13, wherein the chemical modification comprises a replacement of the hydroxyl group at position 2' of ribose of at least one nucleotide included in the lasiRNA molecule by any one of a hydrogen atom, a fluorine atom, an —O-alkyl group, and an amino group.

15. The lasiRNA molecule of claim 13, wherein the chemical modification comprises a replacement of the phosphate backbone of at least one nucleotide included in the lasiRNA molecule by any one of a phosphorothioate form, phosphorodithioate form, alkylphosphonate form, phosphoroamidate form, and boranophosphate form.

16. The lasiRNA molecule of claim 13, wherein the chemical modification comprises a replacement of at least one nucleotide included in the lasiRNA molecule by any one of LNA (locked nucleic acid), UNS (unlocked nucleic acid) morpholino, and PNA (peptide nucleic acid).

17. The lasiRNA molecule of claim 13, wherein the chemical modification comprises a lipid, cell penetrating peptide, or cell targeting ligand bound to the lasiRNA molecule.

18. The lasiRNA molecule of claim 2, wherein a cell delivery vehicle is bound to the lasiRNA molecule.

19. The lasiRNA molecule of claim 18, wherein the cell delivery vehicle is selected from cationic polymers, lipids, cell penetrating peptides, and cell-targeting ligands.

* * * * *

SEQUENCE LISTING

```
<160> NUMBER OF SEQ ID NOS: 35

<210> SEQ ID NO 1
<211> LENGTH: 21
<212> TYPE: RNA
<213> ORGANISM: Artificial Sequence
<220> FEATURE:
<223> OTHER INFORMATION: Sense strand of CTNNB1-2 siRNA

<400> SEQUENCE: 1
cuaucaagau gaugcagaac u                                              21

<210> SEQ ID NO 2
<211> LENGTH: 21
<212> TYPE: RNA
<213> ORGANISM: Artificial Sequence
<220> FEATURE:
<223> OTHER INFORMATION: Antisense strand of CTNNB1-2 siRNA

<400> SEQUENCE: 2
uucugcauca ucuugauagu u                                              21

<210> SEQ ID NO 3
<211> LENGTH: 33
<212> TYPE: DNA
<213> ORGANISM: Artificial Sequence
<220> FEATURE:
<223> OTHER INFORMATION: Dz339 DNAzyme

<400> SEQUENCE: 3
agcatgaaag gctagctaca acgatgtgta gat                                 33
```

```
<210> SEQ ID NO 4
<211> LENGTH: 58
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Dz339 AS hybrid
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(58)
<223> OTHER INFORMATION: deoxyribonucleotides

<400> SEQUENCE: 4
uucugcauca ucuugauagt tttttagcat gaaaggctag ctacaacgat gtgtagat        58

<210> SEQ ID NO 5
<211> LENGTH: 21
<212> TYPE: RNA
<213> ORGANISM: Artificial Sequence
<220> FEATURE:
<223> OTHER INFORMATION: Sense strand of KRAS siRNA

<400> SEQUENCE: 5
ggaagcaagu aguaauugau u                                                21

<210> SEQ ID NO 6
<211> LENGTH: 21
<212> TYPE: RNA
<213> ORGANISM: Artificial Sequence
<220> FEATURE:
<223> OTHER INFORMATION: Antisense strand of KRAS siRNA (19+2)

<400> SEQUENCE: 6
ucaauuacua cuugcuuccu u                                                21

<210> SEQ ID NO 7
<211> LENGTH: 26
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Antisense strand of KRAS lsiRNA (21S+5d)
<220> FEATURE:
<221> NAME/KEY: misc_feature
<222> LOCATION: (1)..(21)
<223> OTHER INFORMATION: ribonucleotides
<220> FEATURE:
<221> NAME/KEY: misc_feature
<222> LOCATION: (22)..(26)
<223> OTHER INFORMATION: deoxyribonucleotides

<400> SEQUENCE: 7
ucaauuacua cuugcuuccu gtagga                                           26

<210> SEQ ID NO 8
<211> LENGTH: 26
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Antisense strand of KRAS lsiRNA (21S+5c)
<220> FEATURE:
<221> NAME/KEY: misc_feature
<222> LOCATION: (1)..(21)
```

```
<223> OTHER INFORMATION: ribonucleotides
<220> FEATURE:
<221> NAME/KEY: misc_feature
<222> LOCATION: (22)..(26)
<223> OTHER INFORMATION: deoxyribonucleotides

<400> SEQUENCE: 8
ucaauuacua cuugcuuccu gagcat                                          26

<210> SEQ ID NO 9
<211> LENGTH: 31
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Antisense strand of KRAS lsiRNA (21S+10d)
<220> FEATURE:
<221> NAME/KEY: misc_feature
<222> LOCATION: (1)..(21)
<223> OTHER INFORMATION: ribonucleotides
<220> FEATURE:
<221> NAME/KEY: misc_feature
<222> LOCATION: (22)..(31)
<223> OTHER INFORMATION: deoxyribonucleotides

<400> SEQUENCE: 9
ucaauuacua cuugcuuccu gtaggaatcc t                                    31

<210> SEQ ID NO 10
<211> LENGTH: 31
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Antisense strand of KRAS lsiRNA (21S+10c)
<220> FEATURE:
<221> NAME/KEY: misc_feature
<222> LOCATION: (1)..(21)
<223> OTHER INFORMATION: ribonucleotides
<220> FEATURE:
<221> NAME/KEY: misc_feature
<222> LOCATION: (22)..(31)
<223> OTHER INFORMATION: deoxyribonucleotides

<400> SEQUENCE: 10
ucaauuacua cuugcuuccu gagcatgacc a                                    31

<210> SEQ ID NO 11
<211> LENGTH: 36
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Antisense strand of KRAS lsiRNA (21S+15d)
<220> FEATURE:
<221> NAME/KEY: misc_feature
<222> LOCATION: (1)..(21)
<223> OTHER INFORMATION: ribonuclotides
<220> FEATURE:
<221> NAME/KEY: misc_feature
<222> LOCATION: (22)..(36)
<223> OTHER INFORMATION: deoxyribonuclotides

<400> SEQUENCE: 11
ucaauuacua cuugcuuccu gtaggaatcc tctatt                               36

<210> SEQ ID NO 12
<211> LENGTH: 36
```

```
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Antisense strand of KRAS lsiRNA (21S+15c)
<220> FEATURE:
<221> NAME/KEY: misc_feature
<222> LOCATION: (1)..(21)
<223> OTHER INFORMATION: ribonucleotides
<220> FEATURE:
<221> NAME/KEY: misc_feature
<222> LOCATION: (22)..(36)
<223> OTHER INFORMATION: deoxyribonucleotides

<400> SEQUENCE: 12
ucaauuacua cuugcuuccu gagcatgacc acggtt                              36

<210> SEQ ID NO 13
<211> LENGTH: 21
<212> TYPE: RNA
<213> ORGANISM: Artificial Sequence
<220> FEATURE:
<223> OTHER INFORMATION: Sense strand of KRAS lsiRNA (21S+15d-mut)

<400> SEQUENCE: 13
ggaagcaagu aguuuaacau u                                              21

<210> SEQ ID NO 14
<211> LENGTH: 36
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Antisense strand of KRAS lsiRNA (21S+15d-mut)
<220> FEATURE:
<221> NAME/KEY: misc_feature
<222> LOCATION: (1)..(21)
<223> OTHER INFORMATION: ribonuclotides
<220> FEATURE:
<221> NAME/KEY: misc_feature
<222> LOCATION: (22)..(36)
<223> OTHER INFORMATION: deoxyribonuclotides

<400> SEQUENCE: 14
uguuaaacua cuugcuuccu gtaggaatcc tctatt                              36

<210> SEQ ID NO 15
<211> LENGTH: 20
<212> TYPE: DNA
<213> ORGANISM: Artificial Sequence
<220> FEATURE:
<223> OTHER INFORMATION: KRAS forward sequence

<400> SEQUENCE: 15
gagtgccttg acgatacagc                                                20

<210> SEQ ID NO 16
<211> LENGTH: 20
<212> TYPE: DNA
<213> ORGANISM: Artificial Sequence
<220> FEATURE:
<223> OTHER INFORMATION: KRAS reverse sequence

<400> SEQUENCE: 16
ccctcattgc actgtactcc                                                20

<210> SEQ ID NO 17
```

```
<211> LENGTH: 16
<212> TYPE: RNA
<213> ORGANISM: Artificial Sequence
<220> FEATURE:
<223> OTHER INFORMATION: Sense strand of KRAS asiRNA

<400> SEQUENCE: 17
agcaaguagu aauuga                                                         16

<210> SEQ ID NO 18
<211> LENGTH: 21
<212> TYPE: RNA
<213> ORGANISM: Artificial Sequence
<220> FEATURE:
<223> OTHER INFORMATION: Antisense strand of KRAS asiRNA

<400> SEQUENCE: 18
ucaauuacua cuugcuuccu u                                                   21

<210> SEQ ID NO 19
<211> LENGTH: 26
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Antisense strand of KRAS lasiRNA (16S+5d)
<220> FEATURE:
<221> NAME/KEY: misc_feature
<222> LOCATION: (1)..(21)
<223> OTHER INFORMATION: ribonuclotides
<220> FEATURE:
<221> NAME/KEY: misc_feature
<222> LOCATION: (22)..(26)
<223> OTHER INFORMATION: deoxyribonuclotides

<400> SEQUENCE: 19
ucaauuacua cuugcuuccu gtagga                                              26

<210> SEQ ID NO 20
<211> LENGTH: 26
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Antisense strand of KRAS lasiRNA (16S+5c)
<220> FEATURE:
<221> NAME/KEY: misc_feature
<222> LOCATION: (1)..(21)
<223> OTHER INFORMATION: ribonuclotides
<220> FEATURE:
<221> NAME/KEY: misc_feature
<222> LOCATION: (22)..(26)
<223> OTHER INFORMATION: deoxyribonuclotides

<400> SEQUENCE: 20
ucaauuacua cuugcuuccu gagcat                                              26

<210> SEQ ID NO 21
<211> LENGTH: 31
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Antisense strand of KRAS lasiRNA (16S+10d)
<220> FEATURE:
<221> NAME/KEY: misc_feature
<222> LOCATION: (1)..(21)
<223> OTHER INFORMATION: ribonucleotides
```

```
<220> FEATURE:
<221> NAME/KEY: misc_feature
<222> LOCATION: (22)..(31)
<223> OTHER INFORMATION: deoxyribonucleotides

<400> SEQUENCE: 21
ucaauuacua cuugcuuccu gtaggaatcc t                                           31

<210> SEQ ID NO 22
<211> LENGTH: 31
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Antisense strand of KRAS lasiRNA (16S+10c)
<220> FEATURE:
<221> NAME/KEY: misc_feature
<222> LOCATION: (1)..(21)
<223> OTHER INFORMATION: ribonucleotides
<220> FEATURE:
<221> NAME/KEY: misc_feature
<222> LOCATION: (22)..(31)
<223> OTHER INFORMATION: deoxyribonucleotides

<400> SEQUENCE: 22
ucaauuacua cuugcuuccu gagcatgacc a                                           31

<210> SEQ ID NO 23
<211> LENGTH: 36
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Antisense strand of KRAS lasiRNA (16S+15d)
<220> FEATURE:
<221> NAME/KEY: misc_feature
<222> LOCATION: (1)..(21)
<223> OTHER INFORMATION: ribonucleotides
<220> FEATURE:
<221> NAME/KEY: misc_feature
<222> LOCATION: (22)..(36)
<223> OTHER INFORMATION: deoxyribonucleotides

<400> SEQUENCE: 23
ucaauuacua cuugcuuccu gtaggaatcc tctatt                                      36

<210> SEQ ID NO 24
<211> LENGTH: 36
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Antisense strand of KRAS lasiRNA (16S+15c)
<220> FEATURE:
<221> NAME/KEY: misc_feature
<222> LOCATION: (1)..(21)
<223> OTHER INFORMATION: ribonucleotides
<220> FEATURE:
<221> NAME/KEY: misc_feature
<222> LOCATION: (22)..(36)
<223> OTHER INFORMATION: deoxyribonucleotides

<400> SEQUENCE: 24
ucaauuacua cuugcuuccu gagcatgacc acggtt                                      36

<210> SEQ ID NO 25
<211> LENGTH: 31
<212> TYPE: RNA
```

```
<213> ORGANISM: Artificial Sequence
<220> FEATURE:
<223> OTHER INFORMATION: Antisense strand of KRAS lasiRNA (21S+10r) or
      lasiRNA (16S+10r)

<400> SEQUENCE: 25
ucaauuacua cuugcuuccu guaggaaucc u                                        31

<210> SEQ ID NO 26
<211> LENGTH: 31
<212> TYPE: RNA
<213> ORGANISM: Artificial Sequence
<220> FEATURE:
<223> OTHER INFORMATION: Antisense strand of KRAS lasiRNA (21S+10rc) or
      lasiRNA (16S+10rc)

<400> SEQUENCE: 26
ucaauuacua cuugcuuccu gagcaugacc a                                        31

<210> SEQ ID NO 27
<211> LENGTH: 21
<212> TYPE: RNA
<213> ORGANISM: Artificial Sequence
<220> FEATURE:
<223> OTHER INFORMATION: Sense strand of CTNNB1-2 siRNA (19+2)

<400> SEQUENCE: 27
cuaucaagau gaugcagaau u                                                   21

<210> SEQ ID NO 28
<211> LENGTH: 21
<212> TYPE: RNA
<213> ORGANISM: Artificial Sequence
<220> FEATURE:
<223> OTHER INFORMATION: Antisense strand of KRAS siRNA (19+2) or asiRNA

<400> SEQUENCE: 28
uucugcauca ucuugauagu u                                                   21

<210> SEQ ID NO 29
<211> LENGTH: 16
<212> TYPE: RNA
<213> ORGANISM: Artificial Sequence
<220> FEATURE:
<223> OTHER INFORMATION: Sense strand of CTNNB1-2 siRNA

<400> SEQUENCE: 29
ucaagaugau gcagaa                                                         16

<210> SEQ ID NO 30
<211> LENGTH: 36
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Antisense strand of KRAS lasiRNA (16S+15d)
<220> FEATURE:
<221> NAME/KEY: misc_feature
<222> LOCATION: (1)..(21)
<223> OTHER INFORMATION: ribonucleotides
<220> FEATURE:
<221> NAME/KEY: misc_feature
<222> LOCATION: (22)..(36)
<223> OTHER INFORMATION: deoxyribonucleotides

<400> SEQUENCE: 30
uucugcauca ucuugauagu uaaucaaguu tacaac                                   36
```

```
<210> SEQ ID NO 31
<211> LENGTH: 36
<212> TYPE: DNA
<213> ORGANISM: Artificial Sequence
<220> FEATURE:
<223> OTHER INFORMATION: Molecule is combined RNA/DNA
<220> FEATURE:
<223> OTHER INFORMATION: Antisense strand of KRAS lasiRNA (16S+15c)
<220> FEATURE:
<221> NAME/KEY: misc_feature
<222> LOCATION: (1)..(21)
<223> OTHER INFORMATION: ribonucleotides
<220> FEATURE:
<221> NAME/KEY: misc_feature
<222> LOCATION: (22)..(36)
<223> OTHER INFORMATION: deoxyribonucleotides

<400> SEQUENCE: 31
uucugcauca ucuugauagu uggagcatga ccacgg                             36

<210> SEQ ID NO 32
<211> LENGTH: 20
<212> TYPE: DNA
<213> ORGANISM: Artificial Sequence
<220> FEATURE:
<223> OTHER INFORMATION: CTNNB1 forward sequence

<400> SEQUENCE: 32
atgtccagcg tttggctgaa                                               20

<210> SEQ ID NO 33
<211> LENGTH: 22
<212> TYPE: DNA
<213> ORGANISM: Artificial Sequence
<220> FEATURE:
<223> OTHER INFORMATION: CTNNB1 reverse sequence

<400> SEQUENCE: 33
tggtcctcgt catttagcag tt                                            22

<210> SEQ ID NO 34
<211> LENGTH: 26
<212> TYPE: DNA
<213> ORGANISM: Artificial Sequence
<220> FEATURE:
<223> OTHER INFORMATION: KRAS Gene specific Primer

<400> SEQUENCE: 34
ctgcatgcac caaaaacccc aagaca                                        26

<210> SEQ ID NO 35
<211> LENGTH: 27
<212> TYPE: DNA
<213> ORGANISM: Artificial Sequence
<220> FEATURE:
<223> OTHER INFORMATION: KRAS Gene Specific Primer Nested

<400> SEQUENCE: 35
cacaaagaaa gccctcccca gtcctca                                       27
```